(12) United States Patent
Takenaka et al.

(10) Patent No.: US 8,792,024 B2
(45) Date of Patent: Jul. 29, 2014

(54) IMAGING SYSTEM AND METHOD FOR ERROR-REDUCTION PROCESSING

(75) Inventors: Katsuro Takenaka, Honjo (JP); Tadao Endo, Honjo (JP); Toshio Kameshima, Kumagaya (JP); Tomoyuki Yagi, Honjo (JP); Keigo Yokoyama, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 444 days.

(21) Appl. No.: 13/286,478

(22) Filed: Nov. 1, 2011

(65) Prior Publication Data

US 2012/0044392 A1 Feb. 23, 2012

Related U.S. Application Data

(62) Division of application No. 12/279,198, filed as application No. PCT/JP2007/055930 on Mar. 15, 2007, now Pat. No. 8,072,514.

(30) Foreign Application Priority Data

Mar. 16, 2006 (JP) .................................. 2006-072934
Jun. 16, 2006 (JP) .................................. 2006-167877
Jan. 17, 2007 (JP) .................................. 2007-008139

(51) Int. Cl.
*H04N 9/64* (2006.01)

(52) U.S. Cl.
USPC ........................................................ 348/246

(58) Field of Classification Search
USPC ............ 348/231.99, 241, 243, 245, 246, 247, 348/251, 220.1; 378/98.8; 250/208.1
See application file for complete search history.

(56) References Cited

U.S. PATENT DOCUMENTS 4,399,464 A * 8/1983 Hix et al. ....................... 348/306
5,970,115 A 10/1999 Colbeth et al. .................. 378/62
(Continued)

FOREIGN PATENT DOCUMENTS

EP 1 777 944 4/2007
JP 61-260772 11/1986
(Continued)

OTHER PUBLICATIONS

Chinese Official Letter dated Sep. 25, 2010, issued in counterpart Chinese Application No. 200780008996.9, with translation.

(Continued)

*Primary Examiner* — Nicholas Giles
(74) *Attorney, Agent, or Firm* — Fitzpatrick, Cella, Harper & Scinto

(57) ABSTRACT

An imaging apparatus is provided, which improves correction accuracy at the time of pixel addition reading and scarcely deteriorates in resolution of the image data. This apparatus comprises: a conversion unit comprising a plurality of unit-pixels and converting an incident radiation or a light into pixel information; a signal processing unit capable of reading the pixel information for each unit-pixel, or capable of reading additional added pixel information for a plurality of unit-pixels, based on a control from a control unit for controlling a driving of the conversion unit according to a plurality of operation modes; a storage unit for storing a plurality of correction information according to the plurality of operating modes; and a correction unit for performing the correction of the pixel information based on the correction information extracted from the plurality of correct information according to the operation mode.

12 Claims, 28 Drawing Sheets

(56) References Cited

U.S. PATENT DOCUMENTS

| | | | |
|---|---|---|---|
| 6,075,256 A | 6/2000 | Kaifu et al. | 257/53 |
| 6,424,750 B1 * | 7/2002 | Colbeth et al. | 382/260 |
| 6,744,912 B2 * | 6/2004 | Colbeth et al. | 382/132 |
| 6,775,351 B2 * | 8/2004 | Rinaldi et al. | 378/98.8 |
| 6,904,126 B2 * | 6/2005 | Endo | 378/98.8 |
| 6,952,015 B2 | 10/2005 | Kameshima | 250/370.11 |
| 6,952,464 B2 | 10/2005 | Endo | 378/98.11 |
| 7,012,260 B2 | 3/2006 | Endo | 250/370.11 |
| 7,016,466 B2 * | 3/2006 | Rinaldi et al. | 378/98.8 |
| 7,031,431 B2 * | 4/2006 | Endo | 378/62 |
| 7,068,313 B2 * | 6/2006 | Karunen et al. | 348/246 |
| 7,113,565 B2 * | 9/2006 | Endo | 378/62 |
| 7,227,926 B2 | 6/2007 | Kameshima et al. | 378/98.9 |
| 7,241,983 B2 * | 7/2007 | Spahn | 250/208.1 |
| 7,342,221 B2 | 3/2008 | Takenaka et al. | 250/252.1 |
| 7,381,963 B2 | 6/2008 | Endo et al. | 250/370.09 |
| 7,386,089 B2 | 6/2008 | Endo et al. | 378/5 |
| 7,403,594 B2 | 7/2008 | Endo et al. | 378/114 |
| 7,408,167 B2 | 8/2008 | Kameshima et al. | 250/370.09 |
| 7,421,063 B2 | 9/2008 | Takenaka et al. | 378/116 |
| 7,532,706 B2 * | 5/2009 | Kameshima et al. | 378/98 |
| 7,629,587 B2 | 12/2009 | Yagi et al. | 250/370.15 |
| 7,742,028 B2 * | 6/2010 | Nitta et al. | 345/88 |
| 7,839,977 B2 | 11/2010 | Kameshima et al. | 378/116 |
| 7,989,772 B2 | 8/2011 | Yagi et al. | 250/370.09 |
| 7,994,481 B2 | 8/2011 | Yagi et al. | 250/370.09 |
| 2004/0017891 A1 * | 1/2004 | Endo | 378/98.8 |
| 2004/0228452 A1 * | 11/2004 | Rinaldi et al. | 378/207 |
| 2005/0184243 A1 * | 8/2005 | Endo | 250/369 |
| 2005/0199834 A1 | 9/2005 | Takenaka et al. | 250/580 |
| 2005/0200720 A1 | 9/2005 | Kameshima et al. | 348/220.1 |
| 2005/0264665 A1 | 12/2005 | Endo et al. | 348/308 |
| 2006/0056588 A1 * | 3/2006 | Endo | 378/62 |
| 2006/0104417 A1 * | 5/2006 | Kameshima et al. | 378/98 |
| 2006/0119719 A1 | 6/2006 | Kameshima | 348/308 |
| 2006/0192130 A1 | 8/2006 | Yagi | 250/370.14 |
| 2007/0040099 A1 | 2/2007 | Yokoyama et al. | 250/208.1 |
| 2007/0096032 A1 | 5/2007 | Yagi et al. | 250/370.11 |
| 2007/0125952 A1 | 6/2007 | Endo et al. | 250/369 |
| 2007/0131843 A1 | 6/2007 | Yokoyama et al. | 250/205 |
| 2007/0210258 A1 | 9/2007 | Endo et al. | 250/370.09 |
| 2007/0291904 A1 | 12/2007 | Takenaka et al. | 378/207 |
| 2008/0011958 A1 | 1/2008 | Endo et al. | 250/370.08 |
| 2008/0013686 A1 | 1/2008 | Kameshima et al. | 378/98 |
| 2008/0029688 A1 | 2/2008 | Yagi et al. | 250/208.1 |
| 2008/0054182 A1 | 3/2008 | Yokoyama et al. | 250/370.09 |
| 2008/0083876 A1 | 4/2008 | Endo et al. | 250/369 |
| 2008/0226031 A1 | 9/2008 | Yokoyama et al. | 378/98.7 |

FOREIGN PATENT DOCUMENTS

| | | |
|---|---|---|
| JP | 05-023551 | 2/1993 |
| JP | 05-145859 | 6/1993 |
| JP | 08-116044 | 5/1996 |
| JP | 10-066686 | 3/1998 |
| JP | 2002-513465 | 5/2002 |
| JP | 2003-172783 | 6/2003 |
| JP | 2006-068512 | 3/2006 |
| WO | 98/24059 | 6/1998 |
| WO | 2006/013975 A1 | 2/2006 |

OTHER PUBLICATIONS

Beuville et al., "High-Performance, Low-Noise, 128-Channel Read-out-Integrated Circuit for Flat-Panel X-Ray Detector Systems", *Proceedings of the SPIE—the International Society for Optical Engineering SPIE—Int. Soc. Opt. Eng USA*, vol. 5368, No. 1, pp. 714-725 (2004), XP008085921.

* cited by examiner

| DEFECTIVE PIXELS | COLUMN | ROW | OUTPUT |
|---|---|---|---|
| A | 2 | 2 | 50% |
| B | 5 | 3 | 70% |
| C | 3 | 5 | 90% |

| DEFECTIVE PIXELS | COLUMN | ROW | OUTPUT |
|---|---|---|---|
| A | 1 | 1 | 87% |
| B | 3 | 2 | 92% |

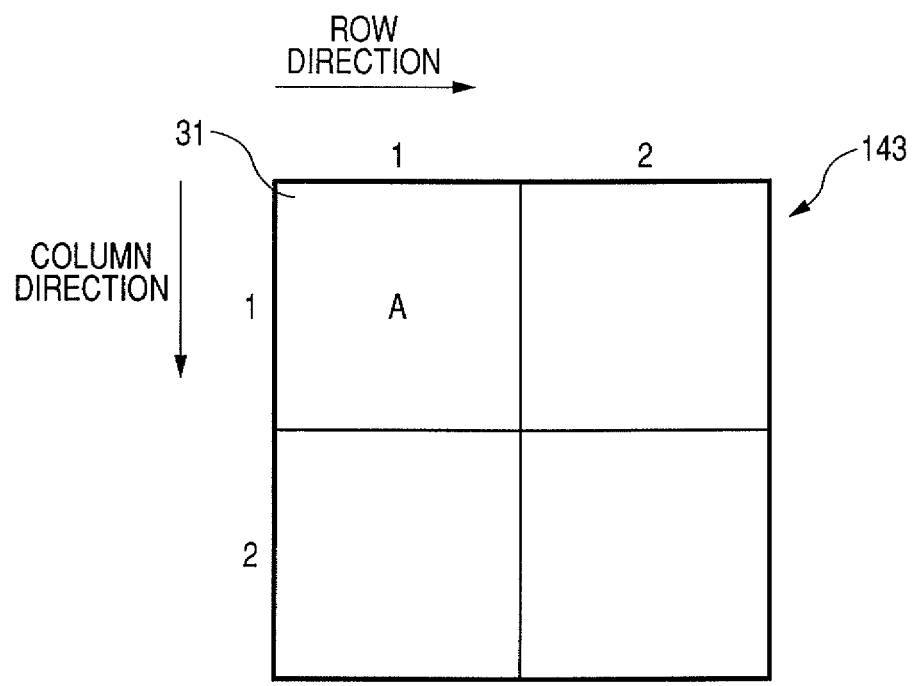

| DEFECTIVE PIXEL | COLUMN | ROW | OUTPUT |
|---|---|---|---|
| B | 4 | 1 | 88% |
| C | 4 | 4 | 84% |

FIG. 19

| OPERATION MODE | PERFORMANCE |
|---|---|
| STILL IMAGE RADIOGRAPHING MODE | |
| MOVING IMAGE RADIOGRAPHING MODE [1] (PIXEL NON-ADDITION MODE) | LOW SPEED/ HIGH RESOLUTION |
| MOVING IMAGE RADIOGRAPHING MODE [2] (2×2 PIXEL-ADDITION MODE) | MIDDLE SPEED/ MEDIUM RESOLUTION |
| MOVING IMAGE RADIOGRAPHING MODE [3] (4×4 PIXEL-ADDITION MODE) | HIGH SPEED/ LOW RESOLUTION |

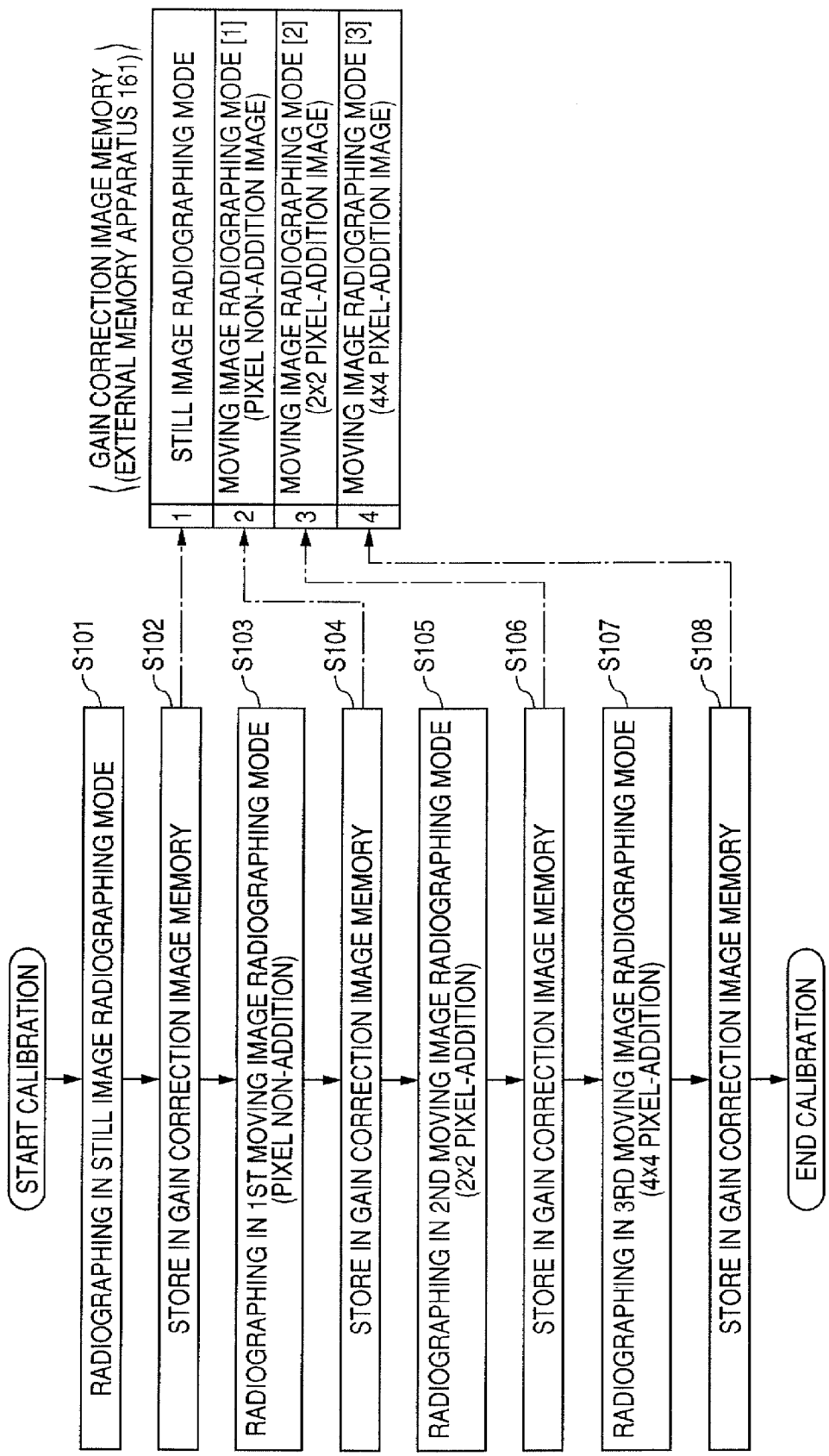

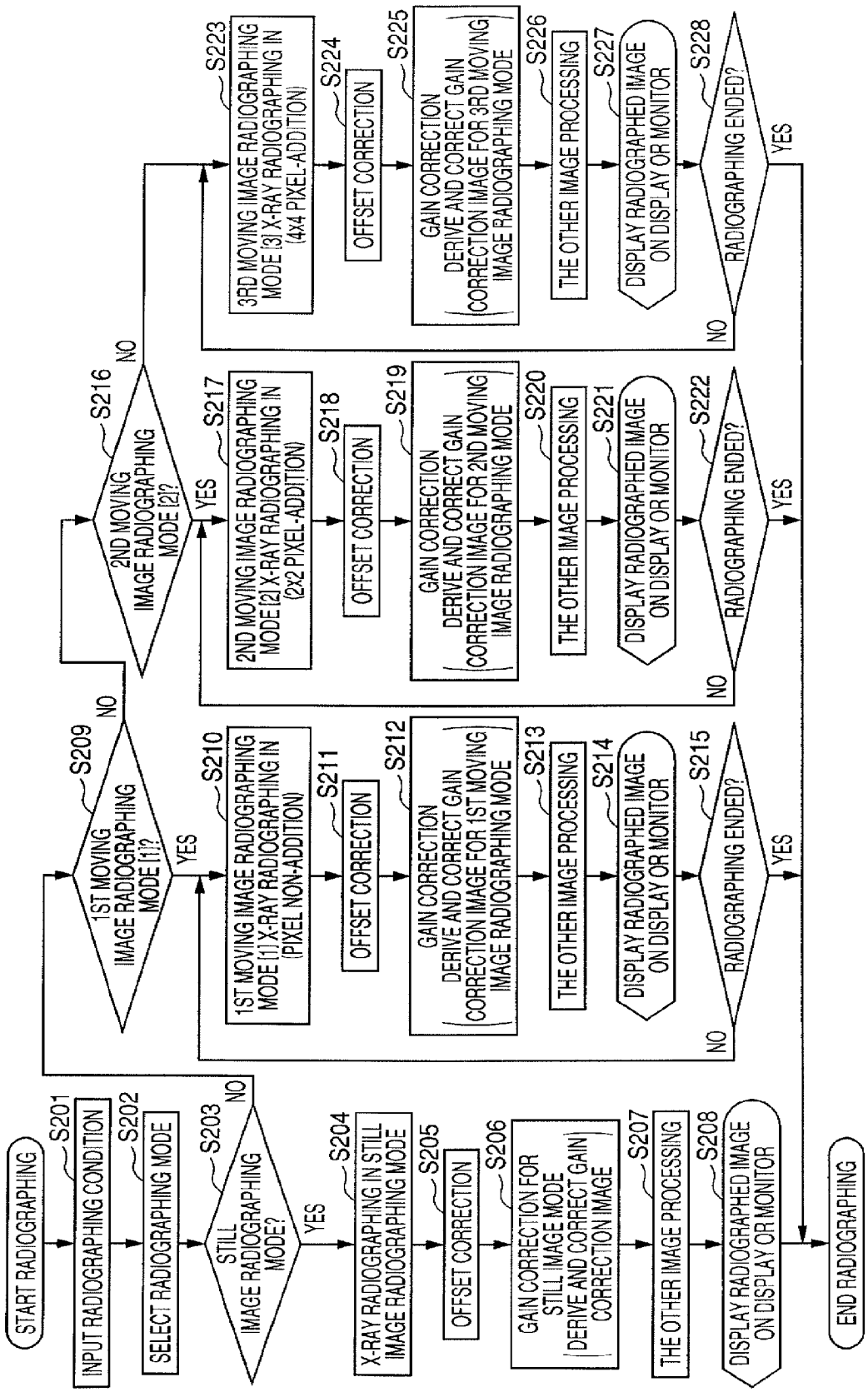

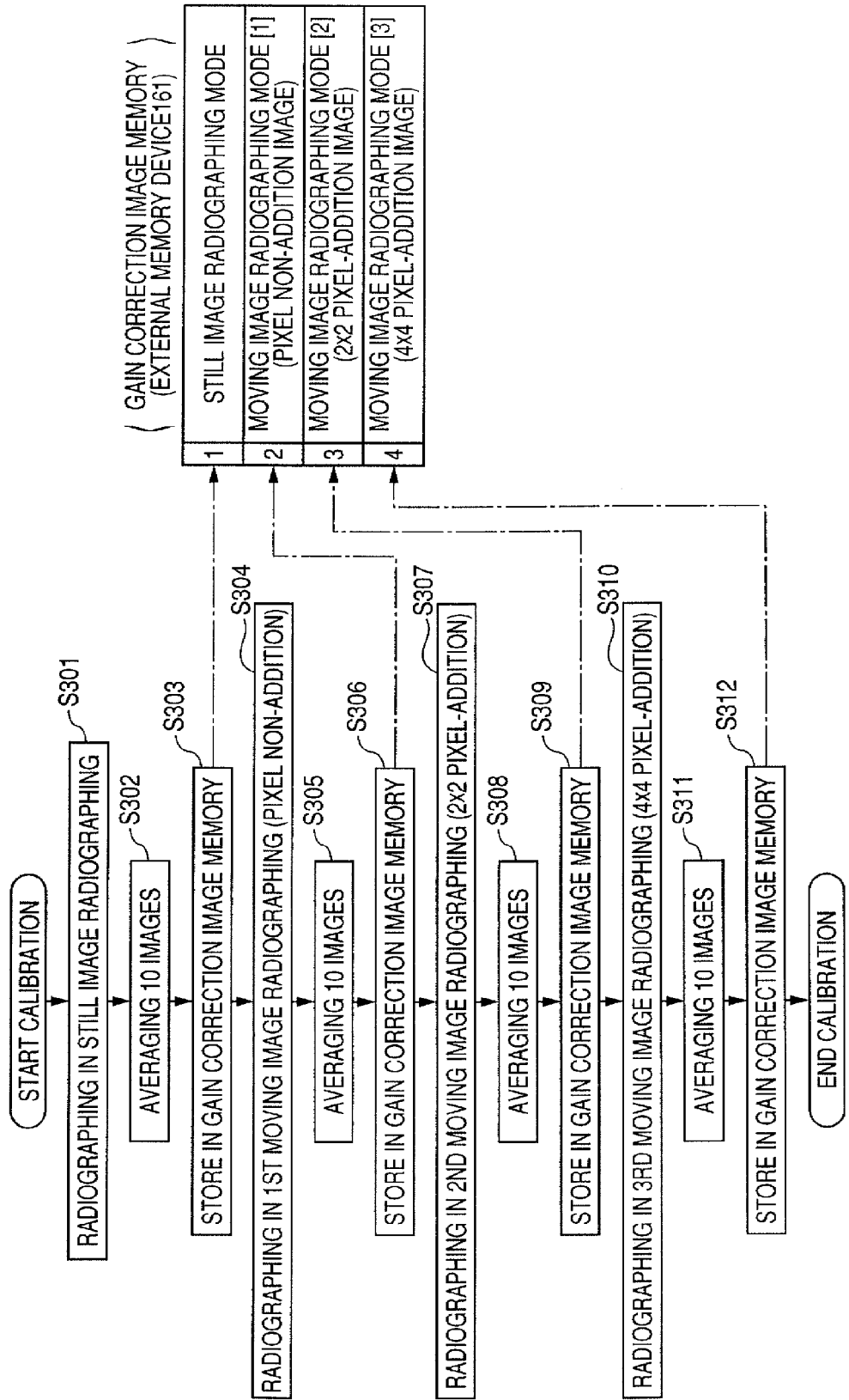

IMAGING SYSTEM AND METHOD FOR ERROR-REDUCTION PROCESSING

RELATED APPLICATIONS

The present application is a divisional of application Ser. No. 12/279,198, filed Aug. 13, 2008, which is a National Stage filing under 35 U.S.C. §371 of International Application No. PCT/JP2007/055930, filed Mar. 15, 2007. The present application claims benefit of parent application Ser. No. 12/279,198 (PCT/JP2007/055930) under 35 U.S.C. §120, and claims priority benefit under 35 U.S.C. §119 from Japanese Patent Applications 2006-072934, filed Mar. 16, 2006, 2006-167877, filed Jun. 16, 2006, and 2007-008139, filed Jan. 17, 2007. The entire contents of each of the mentioned prior applications are incorporated herein by reference.

BACKGROUND OF THE INVENTION

1. Technical Field

The present invention relates to an imaging system applied to a medical diagnostic imaging apparatus, non-destructive inspection apparatus, analytical instrument using radiation, method for processing thereof, and program allowing a computer to execute the method for processing. In particular, the invention relates to the imaging system intending to improve sensitivity and frame rate by pixel-addition and at the same time comprising defect compensating functions. Incidentally, in the present specification, "radiation" also includes electromagnetic waves such as visible light, as well as x-rays, particulate beams such as $\alpha$-rays and $\beta$-rays, and $\gamma$-rays.

2. Background Art

Heretofore, as the still image photography of x-rays in medical treatment, the main stream has been a film system in which x-rays is irradiated on a patient, and its transmitted x-ray image is exposed on a film. The film has functions of displaying and recording information, and can be enlarged to a large area, and is high in gradation, and yet, it is light in weight and can be easily handled. Therefore, it is popularized throughout the world. On the other hand, left behind to be solved are complications requiring development processing, the problem of a location for storing over a long period of time, and the problem of manpower and time required for retrieval.

In the meantime, as a moving image radiography, the main stream has been an image intensifier (hereinafter, abbreviated as [I. I.]). Since the I.I. uses photo-multiplying effect inside the apparatus, in general, sensitivity is high, and it is excellent in view of a low dosage of exposure to radiation. On the other hand, shortcomings such as a distortion of the peripheral image due to optical influences, low contrast, and large size of the apparatus are pointed out. The I.I. has not only the transmitted image of the patient monitored by a doctor, but also can convert an analog output of CCD into a digital signal so as to record, display or store the same. However, since a high gradation is required for diagnosis, even if the I.I. is used for the transmitted image, there are often the cases where the film is used in the still image photography.

In recent years, a demand for digitalization of the x-ray image has been increasing in the hospitals, and in place of the film, an imaging device disposed in a two-dimensional array pattern with a solid state image sensing device converting an electromagnetic wave such as a visible light and radiation into an electrical signal began to be used. This imaging device is called a FPD (Flat Panel Detector) for short.

Since this FPD can substitute x-ray image with digital information, the image information can be transferred far away and instantaneously. Hence, an advantage is also offered in that, while being far away, an advanced diagnosis can be received just as if one were present at a centrally located university hospital. If film is not used, an advantage is also offered in that storage space for the film in the hospital can be eliminated. In the future, if an excellent image data processing technique can be introduced, a potential for an automatic diagnosis by using a computer without intermediary of a radiologist is greatly anticipated.

Further, a radiation imaging apparatus capable of radiographing a still image by using an amorphous silicon thin film semiconductor for the solid state image sensing device has been put to a practical use. As for this radiation imaging apparatus, a large area electronic display exceeding 40 cm square covering the size of a chest region of the human body is realized by using the manufacturing technique of the amorphous silicon thin film semiconductor. Since this manufacturing processing is relatively easy, in the future, realization of an inexpensive radiation imaging apparatus is anticipated. Moreover, since amorphous silicon can be made into a thin glass of not more than 1 mm, an advantage is offered in that the thickness of the detector can be made extremely thin.

Such radiation imaging apparatus is disclosed, for example, in Japanese Patent Application Laid-Open No. H08-116044. Further, in recent years, the radiographing of a moving image by such radiation imaging apparatus is being developed. If one set of such apparatus can be manufactured at a low cost, the still and moving images can be imaged, and therefore, it will be expected to become popular at the great many numbers of hospitals.

When the moving image is imaged by using such radiation imaging apparatus, a problem to be solved is that, as compared with the still image, a reading time is made shorter (frame rate is made faster) and S/N is improved. Hence, when the moving image is radiographed, a driving which is generally called as "pixel-addition" is sometimes performed. Usually, as against reading a single pixel as one pixel (hereinafter, this one pixel is referred to as "unit-pixel"), in the case of the pixel-addition, a plurality of pixels is put together and read as one pixel (hereinafter, this one pixel is referred to as "multi-pixel"). Hence, for example, when two pixels are bound, though the signal is doubled, the noise increase only by ($\sqrt{2}$) times, and therefore, as the S/N, as a S/N of $2/(\sqrt{2})=(\sqrt{2})\approx1.4$ times can be obtained.

Further, the pixel-addition includes a digital-addition and an analog-addition. The digital-addition is read as usual and performs an A/D conversion, and after that, digitally binds up the unit-pixel and constitutes the multi-pixel. In contrast to this, the analog-addition is a technique, in which analog signals are bound up before A/D conversion, and after that, the A/D conversion is performed. The digital-addition is read as usual, and then, performs the A/D conversion, and therefore, though the reading time is not different from the case where the pixel-addition is not performed (hereinafter, referred to as "pixel non-addition", the analog-addition can shorten the reading time.

Further, as for a driving method for addition and reading the unit-pixel in a signal wiring direction, for example, it is disclosed in *Proceedings of SPIE*, Vol. 5368, Item 721, 2004, Eric Beuville, Indigo System Corporation. In this Non-Patent Document, the pixel-addition (averaging out of odd number lines and even number lines) in a signal wiring direction by a sampling and holding circuit unit at the preceding stage of an AD converter (ADC) is performed. The signal is averaged out, and the noise is increased by $1/(\sqrt{2})$ times so that S/N=

($\sqrt{2}$) times. Thus, in the moving image radiographing, the driving by the pixel-addition can be said to be an important method for driving.

Further, though the radiation imaging apparatus performs various image processings for the radiographed image, the basic image processing among them includes an offset correction and gain correction, and a defect-correction. The offset correction is a processing for correcting a dark component of a photoelectrical conversion element and an offset component of a signal processing circuit unit. On the other hand, the gain correction is a processing for correcting the fluctuation in sensitivity of the photoelectric conversion element and the gain fluctuation in the signal processing circuit unit. This gain correction is performed such that, usually before radiographing an object, x-rays is irradiated in a state in which no object exists, thereby performing radiographing, and by using the radiographed image as an image for gain correction, a division processing is performed for the image in which the object is radiographed, so that the correction is performed.

Further, the defect correction is a processing for correcting the pixel value of a defective pixel by using the pixel value of the defective pixel periphery. Although such radiation imaging apparatus comprises a semiconductor, when manufacturing the apparatus, due to a defect caused in the semiconductor and an influence of the dust adhered in the manufacturing process, there are often the cases where a defect is caused in the pixel. To manufacture the whole of a great many number of pixels comprising the radiation imaging apparatus without causing any defect is extremely difficult. Consequently, if the imaging apparatus including the defective pixel is not used, this will invite a reduction in yield ratio of the imaging apparatus. However, if the imaging apparatus including the defective pixel is used as it is, the quality of the image obtained by the radiographing is remarkably deteriorated due to the influence of the defective pixel.

Hence, in order to use the imaging apparatus including the defective pixel, heretofore, a correction technique for the defect pixel has been proposed. For example, the technique disclosed in Japanese Patent Publication No. H05-023551 corrects the defect by using an average rate of the pixel value in the periphery of the defective pixel.

SUMMARY OF THE INVENTION

However, particularly with respect to the gain correction and the defect correction, when such pixel-addition reading is performed, even when the correction used in case of performing the pixel non-addition reading is performed as it is, there has been a problem in that the correction is not effectively performed.

The present invention has been carried out in view of the above described problem, and aims at providing an imaging apparatus, method for processing, and program, which improve correction accuracy at the time of pixel-addition reading and scarcely deteriorates in resolution of image data.

An imaging apparatus according to one aspect of the invention comprises:

a conversion unit comprising a plurality of unit-pixels for converting, into a signal, incident radiation or light according to the incident radiation or light;

a control unit for controlling said conversion unit according to a plurality of operation modes;

a signal processing unit, operating based on the control by said control unit, for reading a signal of unit-pixel from said conversion unit according to a unit-pixel reading mode among the plurality of operation modes, and for reading a signal of multi-pixel derived by adding signals of two or more unit-pixels from said conversion unit according to a pixel-addition reading mode among the plurality of operation modes;

a storage unit for storing positional information of a defective unit-pixel detected based on comparing, with a first threshold value, a signal of a unit-pixel read by the signal processing unit from said conversion unit irradiated with radiation or light, and for storing positional information of a defective multi-pixel detected based on comparing, with a second threshold value, a signal of a multi-pixel derived by adding signals of two or more unit-pixels read by said signal processing unit from said conversion unit irradiated with radiation or light; and a pixel processing unit for performing a correction of a signal of unit-pixel read by said signal processing unit from the conversion unit, based on the positional information of the defective unit-pixel in the unit-pixel reading mode, and for performing a correction of a signal of multi-pixel derived by adding signals of two or more unit-pixels read by said signal processing unit from said conversion unit, based on the positional information of the defective multi-pixel in the pixel-addition reading mode.

Further, in the imaging apparatus of the present invention, the storage unit comprises unit-pixel defect information which is defect information regarding the unit-pixel and the multi-pixel defect information which is defect information regarding the multi-pixel. The correction unit performs correction based on the unit-pixel defect information for the pixel information which is converted in the conversion unit according to the plurality of operation modes and read for each unit-pixel in the signal processing unit or performs correction based on the multi-pixel defect information for the pixel information which is converted in the conversion unit and read for each multi-pixel in the signal processing unit.

Further, in the imaging apparatus of the present invention, the storage unit comprises correction information for a plurality of gain corrections which are converted in the conversion unit in a state in which no object exists and read by the signal processing unit for each plurality of operation modes, and the correction unit extracts the correction information for the corresponding gain correction from the storage unit according to the plurality of operation modes, and performs the gain correction of an object image based on the pixel information by using the correction information for the gain correction.

According to another aspect of the invention, an imaging apparatus comprises:

a conversion unit comprising a plurality of unit-pixels for converting, into a signal, incident radiation or light according to the incident radiation or light;

a control unit for controlling said conversion unit according to a plurality of operation modes;

a signal processing unit, operating based on the control by said control unit, for reading a signal of unit-pixel from said conversion unit according to a unit-pixel reading mode among the plurality of operation modes, and for reading a signal of multi-pixel derived by adding signals of two or more unit-pixels from said conversion unit according to a pixel-addition reading mode among the plurality of operation modes;

a storage unit for storing positional information of a defective unit-pixel detected based on comparing, with a first threshold value, a signal of unit-pixel read by said signal processing unit from said conversion unit irradiated with radiation or light, and for storing positional information of a defective multi-pixel derived based on comparing, with a second threshold value smaller than the first threshold value, the signal of the unit-pixel; and a pixel processing unit for performing a correction of a signal of a unit-pixel read by said signal processing unit from said conversion unit, based on the positional information of the defective unit-pixel in the unit-pixel reading mode, and for performing a correction of a signal of a multi-pixel derived by adding signals of two or more unit-pixels read by said signal processing unit from said conversion unit, based on the positional information of the defective multi-pixel in the pixel-addition reading mode.

According to one aspect of the invention, a processing method for use in an imaging apparatus that comprises a conversion unit comprising a plurality of unit-pixels for converting, into a signal, an incident radiation or light according to the incident radiation, a control unit for controlling the conversion unit according to a plurality of operation modes, a signal processing unit, operating based on the control by the control unit, for reading a signal of unit-pixel from the conversion unit, and for reading a signal of multi-pixel derived by adding signals of two or more unit-pixels from the conversion unit, and a storage unit for storing positional information of a defective unit-pixel detected based on comparing, with a first threshold value, a signal of unit-pixel read by the signal processing unit from the conversion unit irradiated with radiation or light, and for storing positional information of a defective multi-pixel detected based on comparing, with a second threshold value, a signal of multi-pixel derived by adding signals of two or more unit-pixels read by the signal processing unit from the conversion unit irradiated with radiation or light, wherein the method comprises steps of:

performing a correction of a signal of unit-pixel read by the signal processing unit from the conversion unit, based on the positional information of the defective unit-pixel in an unit-pixel reading mode among a plurality of operation modes; and performing a correction of a signal of multi-pixel derived by adding signals of two or more unit-pixels read by the signal processing unit from the conversion unit, based on the positional information of defective multi-pixel in a pixel-addition reading mode among a plurality of operation.

According to another aspect, a method a for use in an imaging apparatus that comprises a conversion unit comprising a plurality of unit-pixels for converting, into a signal, incident radiation or light according to the incident radiation or light, a control unit for controlling the conversion unit according to a plurality of operation modes, a signal processing unit, operating based on the control by the control unit, for reading a signal of a unit-pixel from the conversion unit, and for reading a signal of a multi-pixel derived by adding signals of two or more unit-pixels from the conversion unit, and a storage unit for storing positional information of a defective unit-pixel detected based on comparing, with a first threshold value, a signal of a unit-pixel read by the signal processing unit from the conversion unit irradiated with radiation or light, and for storing positional information of a defective multi-pixel derived based on comparing, with a second threshold value smaller than the first threshold value, the signal of a unit-pixel, wherein the method comprises steps of:

performing a correction of a signal of a unit-pixel read by the signal processing unit from the conversion unit, based on the positional information of the defective unit-pixel in a unit-pixel reading mode among the plurality of operation modes; and performing a correction of a signal of a multi-pixel derived by adding signals of two or more unit-pixels read by the signal processing unit from the conversion unit, based on the positional information of a defective multi-pixel in a pixel-addition reading mode among the plurality of operation modes.

A non-transitory computer-readable storage medium may be used to store executable code for causing a computer to execute any of the methods that form various aspects of the invention.

Further features of the present invention will become apparent from the following description of exemplary embodiments with reference to the attached drawings.

BRIEF DESCRIPTION OF THE DRAWINGS

FIGS. 11A and 11B are views illustrating a defective multi-pixel when the radiation imaging apparatus of FIG. 2 is read by the nine-pixel-addition mode and one example of the multi-pixel defect coordinate table by the nine-pixel-addition.

FIG. 19 is a view illustrating an operation mode of the radiation imaging system according to the fourth embodiment.

FIG. 25 is a flowchart illustrating an acquisition process of the image for gain correction of the radiation imaging system according to the fourth embodiment.

FIG. 26 is a flowchart illustrating a processing in the radiographing operation of the radiation imaging system according to the fourth embodiment.

FIG. 27 is a flowchart illustrating the acquisition process of the image for gain correction of the radiation imaging system according to a fifth embodiment.

BEST MODE FOR CARRYING OUT THE INVENTION

In the first to third embodiments illustrated below, a defect correction when a pixel-addition is performed will be described. The problem area of the defect correction when the pixel-addition found by the present inventors is performed will be described below.

When pixel-addition reading is performed in the radiation imaging apparatus of the present invention, in case even one pixel of the defective pixel is included in each unit-pixel among multi-pixel, these multi-pixels become defective pixels. Hence, assuming that a conventional defect correction technique is applied, information on the adjacent multi-pixels are appropriated for (substituted for) these defective multi-pixels.

In this case, despite the fact that non-defective but effective pixels are included as unit-pixels even within the defective multi-pixels, the effective pixels are bound to the information on the defective pixels and read by the pixel-addition reading, and therefore, information on these non-defective but effective pixels becomes invalidated. For example, in the case of the four-pixel-addition reading, its defect is a defect of the four-pixels, and lack of information is large. In this case, the correction of the defective multi-pixel was performed not by the adjacent unit-pixel closest to the defect unit-pixel but by information on an adjacent multi-pixel, farther away. As a result, there has been a problem in that the deterioration of the resolution in the image ends up becoming worse.

Hence, a first aspect of the invention of the present application according to the first, second and third embodiments has been carried out in view of the above described problem, and aims at providing an imaging system, the method for processing and program thereof capable of reducing the defective pixel at the time of the pixel-addition reading and having a larger number of pixel information in the image data and scarcely deteriorating in the resolution of the image data.

Embodiments of the first aspect of the invention of the present application will be described below.

First Embodiment

Figure 1:
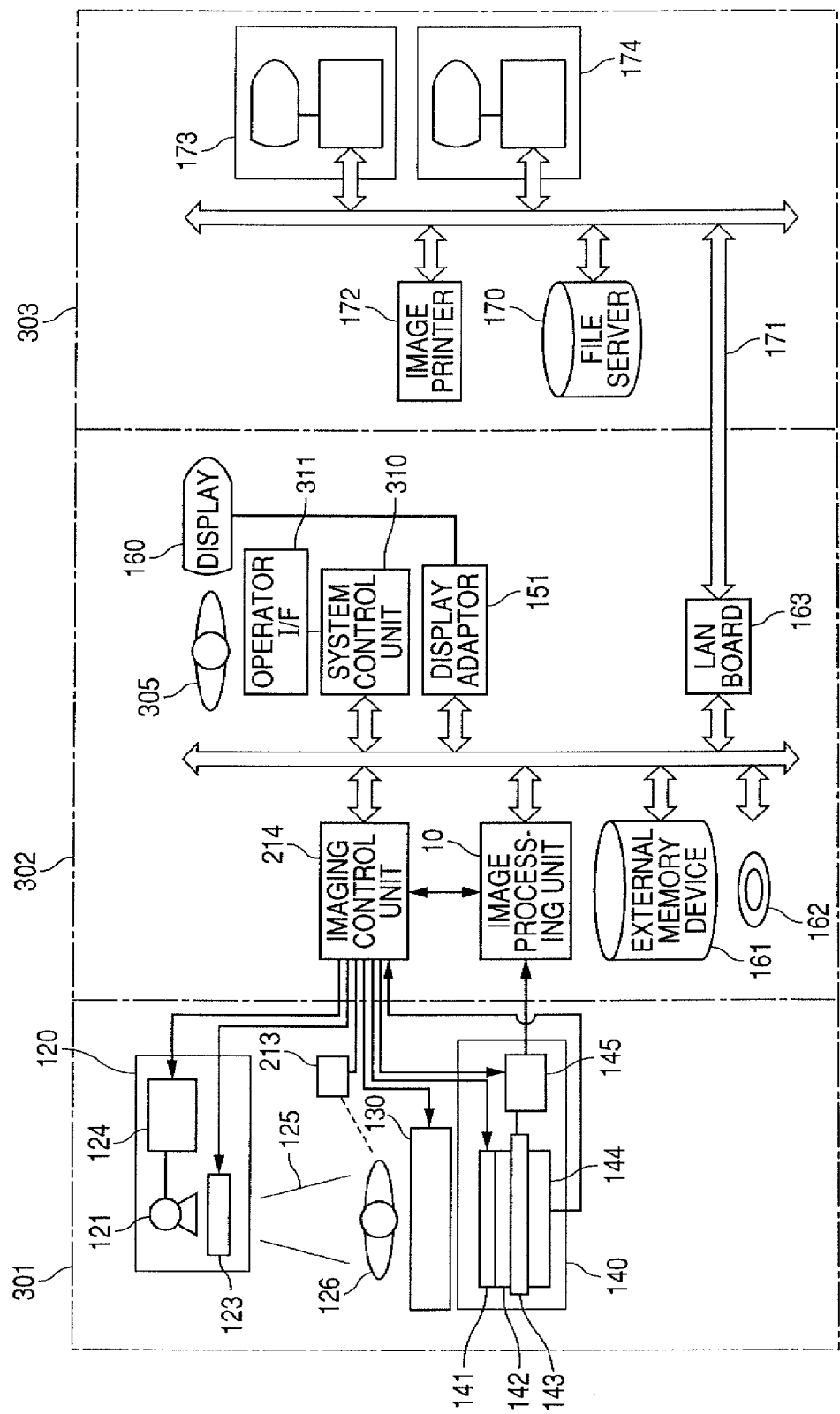
FIG. 1 is a schematic block diagram of a radiation imaging system according to a first embodiment.

FIG. 1 is a schematic block diagram of a radiation imaging system according to a first embodiment. As illustrated in FIG. 1, the radiation imaging system of the present embodiment comprises an x-ray room 301, an x-ray control room 302, and a dispensary 303.

The operation of the radiation imaging system of the present embodiment is controlled by a system control unit 310. An operator interface (I/F) 311 comprises a touch panel on a display, mouse, keyboard, joy stick, foot switch, which are suitably selected by an operator 305. By this operator interface (I/F) 311, a setting of each information such as radiographing conditions (still image, moving image, tube voltage, tube current, irradiating time, and the like), radiographing timing, image processing condition, test subject ID, and method for processing an takeout image can be performed. However, since almost all pieces of information are transferred from a radiation information system (not illustrated), there is no need to input them individually. The important operation of the operator 305 is an operation to confirm the radiographed image. That is, determination is made as to if its angle is correct, if the patient is moving or if the image processing is appropriate and the like.

The system control unit 310 instructs a radiographing condition based on the instruction from the operator 305 or the radiation information system (not illustrated) to an imaging control unit 214 which presides over the x-ray radiographing sequence, and controls the unit 214 so as to take in the image data. The imaging control unit 214, based on the instruction from this system control unit 310, allows a radiation generating apparatus 120 which is a radiation source, bed 130 for radiographing, and radiation imaging apparatus 140 to be operated so as to take in the image data, thereby transferring it to an image processing unit 10.

After transferring this image data, for example, the system control unit 310 allows an image processing designated by the operator 305 to be performed by the image processing unit 10, and this is displayed in a display unit 160. At the same time, the system control unit 310 allows the basic image processing such as offset correction, white correction, defect correction to be performed by the image processing unit 10, and stores the image data after the processing in an external memory device 161. Further, based on the instruction by the operator 305, the system control unit 310 performs a re-radiographing processing and reply displaying, transfer and storage of the image data to the apparatus on a network, display on a display unit, printing on a film, and the like.

Next, the configuration and operation of the radiation imaging system of the present embodiment will be described along a signal flow.

The radiation generating apparatus 120 comprises by including x-ray tube 121, x-ray aperture 123, and high voltage generating power source 124. The x-ray tube 121 is driven by the high voltage generating power source 124 controlled by the imaging control unit 214, and radiates x-ray beam 125.

X-ray aperture 123 is driven by the imaging control unit 214, and forms the x-ray beam 125 so as not to perform unnecessary x-ray irradiation accompanied with a change in the radiographing region. The x-ray beam 125 is directed to a subject 126 lying down on a bed 130 for radiographing having x-ray transmittance.

The bed 130 for radiographing is driven based on a control of the imaging control unit 214. The x-ray beam 125 irradiated from the radiation generating apparatus 120 transmits the subject 126 and the bed 130 for radiographing, and after that, is irradiated on the radiation imaging apparatus 140.

The radiation imaging apparatus 140 comprises by including a grid 141, converter 142, photoelectric conversion circuit unit 143, radiation exposure monitor 144, and external circuit unit 145.

The grid 141 reduces the influence of the x-ray scattering caused by its transmission through the subject 126. This grid 141 comprises x-ray low absorption material and x-ray high absorption material, and for example, it has a stripe structure by Al and Pb. The imaging control unit 214 vibrates the grid 141 so that moiré is not caused by the relationship of a grid ratio between the photoelectric conversion circuit unit 143 and the grid 141 at the x-ray irradiating time.

The wavelength converter 142 includes a phosphor comprising one type selected from $Gd_2O_3$, $Gd_2O_2S$, $CaWO_4$, $CdWO_4$, CsI, and ZnS as a main ingredient. In the wavelength converter 142, a main ingredient material of the phosphor is excited by the incident x-rays of high energy, and outputs fluorescent radiation of a visible region by re-addition energy when re-addition. Its fluorescent radiation is attributed to the main ingredient material itself such as $Gd_2O_3$, $Gd_2O_2S$, $CaWO_4$, $CdWO_4$ and is attributed to a fluorescent radiation central material activated inside the main ingredient material such as CsI:Tl and Zns:Ag. Adjacent to this wavelength converter 142, the photoelectric conversion circuit unit 143 is disposed.

The photoelectric conversion circuit unit 143 converts photons of the light converted into wavelength by the wavelength converter 142 into electric signals by each pixel (unit-pixel) including each conversion element. That is, the photoelectric conversion circuit unit 143 radiographs a radiation image of the subject 126.

The x-ray exposure monitor 144 monitors x-ray transmission. The x-ray exposure monitor 144 may directly detect the x-rays by using a light receiving element such as crystal silicon or may detect light from the wavelength converter 142. In the present embodiment, the visible light (light proportional to the x-ray image) transmitting the photoelectric conversion circuit unit 143 is detected by an amorphous silicon light receiving element of the x-ray exposure monitor 144 deposited on the rear surface of the photoelectric conversion circuit unit 143, and this information is transmitted to the imaging control unit 214. The imaging control unit 214, based on the information from the x-ray exposure monitor 144, drives the high voltage generating power source 124 so as to shut out or adjust the x-rays.

The external circuit unit 145 comprises by including a driving circuit unit for driving the photoelectric conversion circuit unit 143 and a signal processing circuit unit for reading a signal from each pixel of the photoelectric conversion circuit unit 143. This external circuit unit 145, under the control of the imaging control unit 214, drives the photoelectric conversion circuit unit 143, and reads the signal from each pixel, and outputs it as an image signal (image data).

The image signal outputted from the radiation imaging apparatus 140 is transmitted to the image processing unit 10 inside the x-ray control room 302 from the x-ray room 301. At this transmission time, the inside of the x-ray room 301 is filled with a loud noise accompanied with the x-ray generation, and there are sometimes cases where the image signal is not accurately transmitted because of the noise. Hence, it is necessary to improve the protection of the transmission route from noise. For example, provision of a transmission route having an error correction function and use of a transmission route by a pair twisting wire with shield and an optical fiber are desirable.

The image processing unit 10, based on the instruction from the imaging control unit 214, switches over the display data. Further, the image processing unit 10 performs in real time various correction processings such as an offset correction, white correction, and defect correction as well as space filtering processing, and recursive processing, and moreover, performs a gradation processing, scattered radiation correction processing, and various space frequency processing according to needs.

The image data processed by the image processing unit 10 is displayed on a display unit 160 as an image through a display adaptor 151. Further, the basic image data subjected to the correction processing only of the image data at the same time as a real time image processing is stored in an external memory device 161. As the external memory device 161, a data storage device filling a large capacity, high speed, and high reliability is desirable, and for example, a hard disk array such as RAID is desirable. Further, based on the instruction from the operator 305, the image data stored in the external memory device 161 is stored in the other external memory device. At that time, the image data is reconfigured to meet the predetermined standard (for example, IS&C), and after that, it is stored in the other external memory device. As the other external memory device, for example, there exist a magneto-optical disk 162 and hard disk inside a file server 170 on a LAN, and the like.

The radiation imaging system of the present embodiment can be also connected to a LAN 171 through a LAN board 163, and is configured to have compatibility of data with HIS. This LAN 171 is connected with a monitor 174 for displaying a moving image or still image, the file server 170 for filing the image data, an image printer 172 for outputting the image to the film, image processing terminal 173 for performing a complicated image processing and diagnostic support, and the like. Incidentally, it goes without saying that this LAN 171 can be connected with a plurality of radiation imaging systems. Further, the radiation imaging system in the present embodiment outputs the image data according to the predetermined protocol (for example, DICOM). In addition, the radiation imaging system can perform a real time remote diagnosis by a doctor by using the monitor 174 connected to the LAN 171 at radiographing time.

Figure 2:
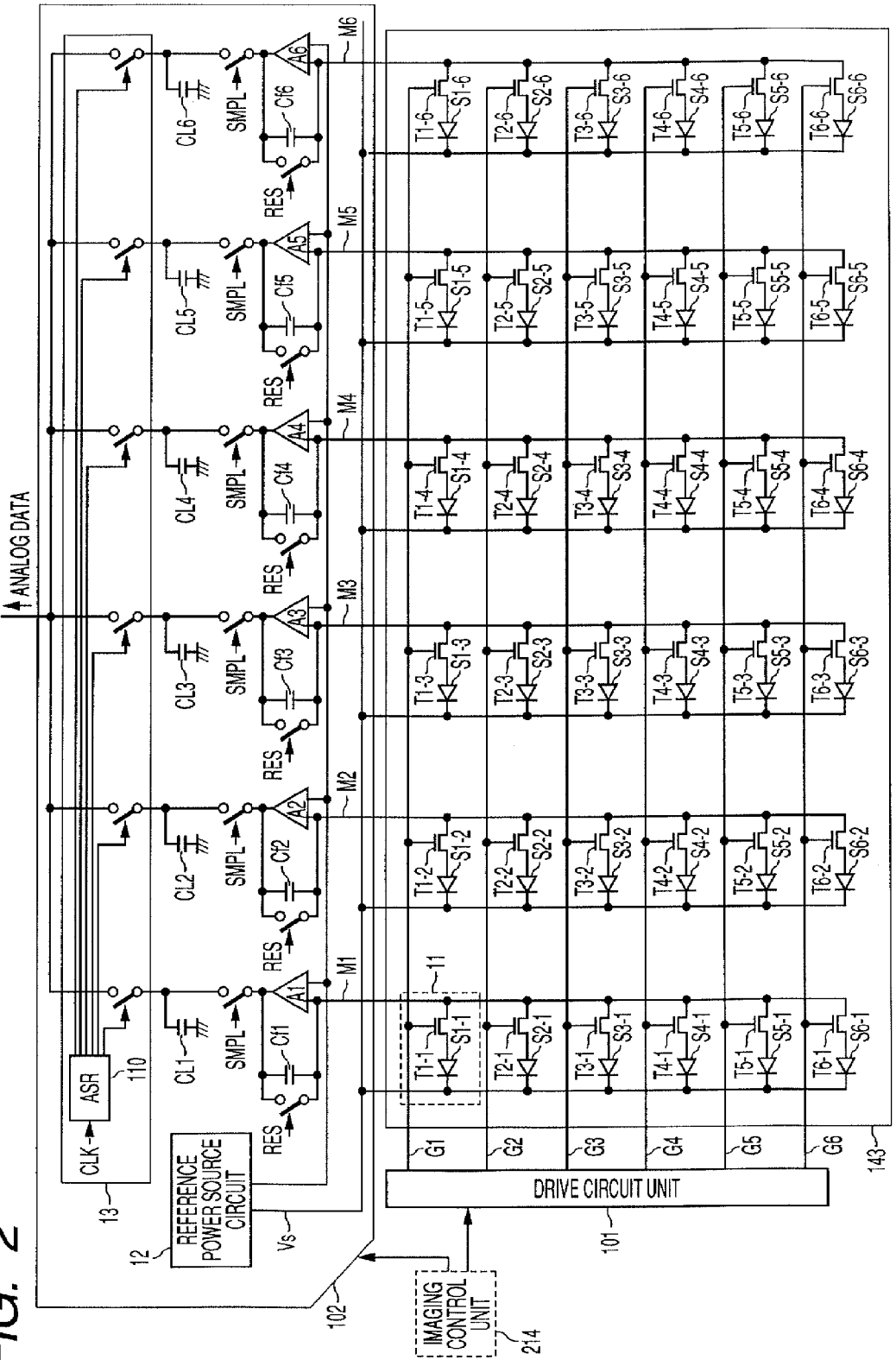
FIG. 2 is an equivalent circuit diagram illustrating a detailed configuration of a radiation imaging apparatus.

Next, the detail of the radiation imaging apparatus 140 will be described. FIG. 2 is an equivalent circuit diagram illustrating the detailed configuration of the radiation imaging apparatus 140. Here, in FIG. 2, from among each component part comprising the radiation imaging apparatus 140, the photoelectric conversion circuit unit 143 and a driving circuit unit 101 provided in the external circuit unit 145 as well as a signal processing circuit unit 102 are illustrated.

This radiation imaging apparatus 140, based on a control from the imaging control unit 214, is configured to be able to drive in various radiographing modes including a moving image radiographing mode, a still image radiographing mode, the pixel reading mode in the unit-pixel reading and pixel-addition reading.

The photoelectric conversion circuit unit 143 of FIG. 2 is disposed in a two-dimensional procession (two-dimensional matrix) with pixels (unit-pixel) 11 comprising one piece each of conversion elements S1-1 to S6-6 which convert radiation into electric charges and switch elements T1-1 to T6-6 which take out the electric charges from the conversion elements. In FIG. 2, for convenience, a total of 36 unit-pixels of six by six pixels are illustrated.

This photoelectric conversion circuit unit 143 is, for example, formed on an insulating substrate such as glass by using an amorphous silicon thin film semiconductor, and the conversion elements S1-1 to S6-6 are formed by a MIS type structure based on amorphous silicon as a main ingredient. In this case, on the conversion elements S1-1 to S6-6, the wavelength converter 142 in which the conversion element converts radiation into a light of the detectable wavelength region is provided, and the conversion element is incident with a visible light from the wavelength converter 142. Incidentally, the conversion elements S1-1 to S6-6 may be those absorbing the incident radiation (x-rays) and converting it directly into an electric charge. As the main ingredient of the conversion element of this direct conversion type, for example, amorphous selenium, gallium arsenide, mercuric iodide, lead iodide or cadmium telluride can be cited. Further, as the switch elements T1-1 to T6-6, a TFT (thin film transistor) formed on the insulating substrate such as glass by amorphous silicon is suitably used.

The conversion elements S1-1 to S6-6 comprise photodiodes, and are applied with a reverse bias. That is, the cathode electrode side of the photodiode is biased to + (plus). A bias wire Vs is a common wire, and is connected to a reference power source circuit 12.

The drive wires G1 to G6 connect the switch element of each pixel in a row direction. The signal wires M1 to M6 connects the switch element of each pixel in a column direction. The drive circuit unit 101 supplies a drive signal (pulse) to each of the gate wires G1 to G6 so as to drive each switch element, and drive-controls each of the conversion elements S1-1 to S6-6.

The signal processing circuit unit 102 amplifies the electric charge outputted in parallel for every row from each pixel through each of the signal wires M1 to M6, and subjects it to series conversion so as to output it as an analog data (image data). The signal processing circuit unit 102 comprises by including amplifiers A1 to A6 provided with capacitors Cf1 to Cf6 provided between input and output terminals, respectively, various switches, sampling and holding circuit comprising capacitors CL1 to CL6, reference power source circuit 12, and analog multiplexer 13.

A switch RES is for resetting the capacitors Cf1 to Cf6. The amplifiers A1 to A6 is for amplifying the signal charges from the signal wires M1 to M6. The capacitors CL1 to CL6 are sampling and holding capacitors for temporarily storing the signal charges amplified by the amplifiers A1 to A6. A switch SMPL is for performing a sampling and holding. The analog multiplexer (MUX) 13 is for directly converting the signal charge outputted in parallel, and comprises by including an analog shift resistor (ASR) 110.

The imaging control unit 214, according to the photographing condition instructed from the system control unit 310, supplies a clock signal CLK to the analog shift resistor 110 in the analog multiplexer 13 of the signal processing circuit unit 102. This clock signal CLK is a signal for allowing the analog shift resistor 110 to be shifted.

Figure 3:
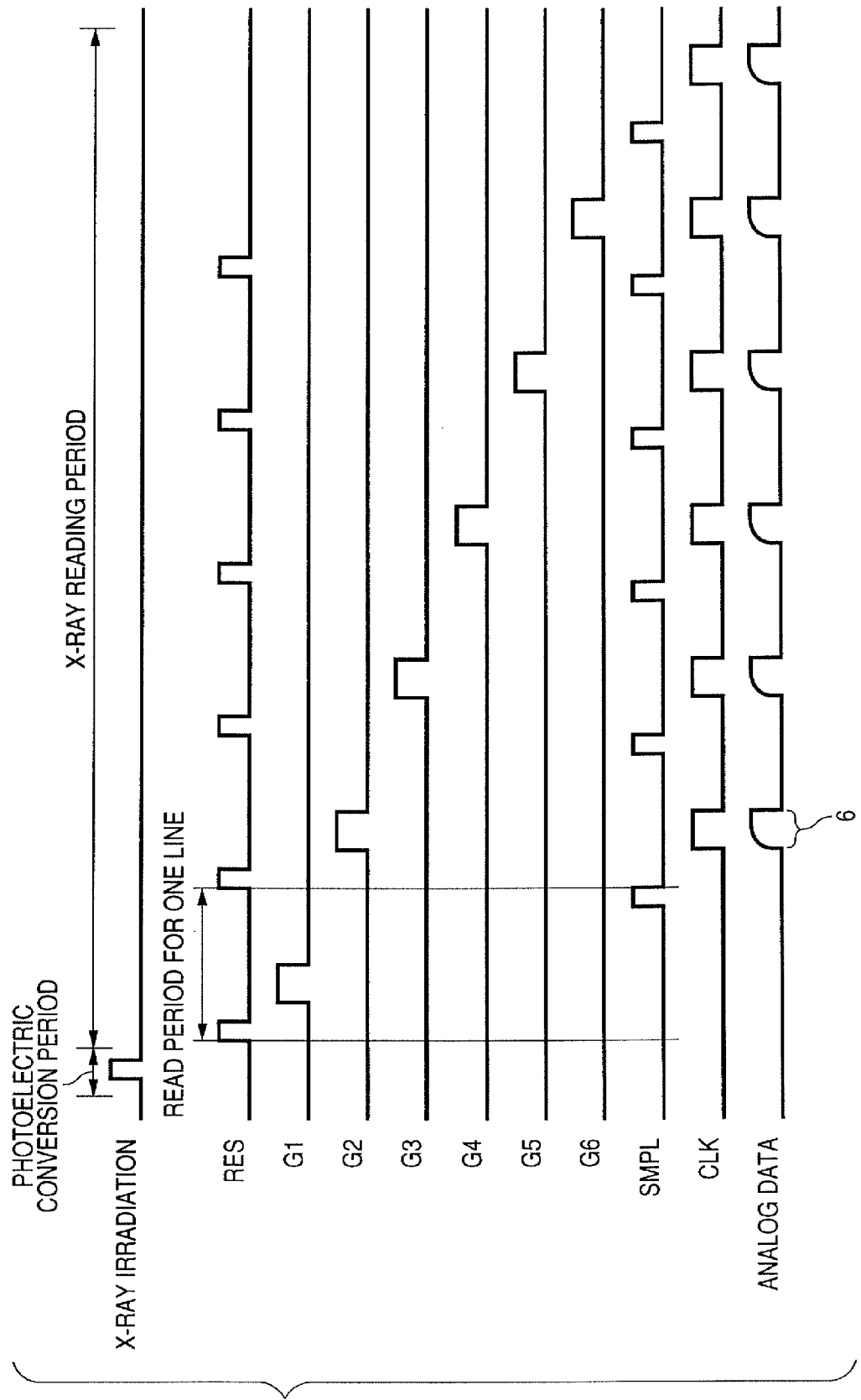
FIG. 3 is a timing chart illustrating a first method for driving (unit-pixel reading mode) the radiation imaging apparatus.

FIG. 3 is a timing chart illustrating a first method for driving (unit-pixel reading mode) of the radiation imaging apparatus 140. Based on this timing chart, the operations of the photoelectric conversion circuit unit 143, drive circuit unit 101, and signal processing circuit unit 102 illustrated in FIG. 2 will be described.

First, the operation in a photoelectric conversion period (x-ray irradiation period) will be described. In a state in which all the switch elements are turned off, when radiation (x-rays) is irradiated pulse-wise from the radiation generating apparatus 120, radiation or a light subjected to wavelength conversion from radiation is irradiated on each conversion element, and signal electric charge corresponding to radiation or a light quantity is accumulated in each conversion element.

At this time, when the above described wavelength conversion member 143 which converts the x-rays into a visible light is used, a member guiding the visible light corresponding to the x-ray dose rate to the conversion element side may be used or the wavelength conversion member 143 may be disposed in the extreme vicinity of the conversion element. Incidentally, even after a light source is turned off, the signal charge subjected to photoelectrical conversion is held in each conversion element.

Next, the operation in the reading period will be described. The reading operation is performed in order for the conversion elements S1-1 to S1-6 of a first line, the conversion elements S2-1 to S2-6 of a second line, and the conversion elements S3-1 to S3-6 of a third line, and it is performed until the reading operation of the conversion elements S6-1 to S6-6 of a sixth line.

First, to read the signal charges accumulated in the conversion elements S1-1 to S1-6 of the first line, a drive signal is given to the drive wire G1 connected to the switch elements T1-1 to T1-6 of a first line from the drive circuit unit 101. At this time, the drive circuit unit 101, based on a control from the imaging control unit 214, outputs the drive signal to the drive wire G1. As a result, the switch elements T1-1 to T1-6 of the first line are put into a turned on state, and the signal charges accumulated in the conversion elements S1-1 to S1-6 of the first line are transferred through the signal wires M1 to M6.

These transferred signal charges are amplified by the amplifiers A1 to A6 according to the capacitance of the capacitors Cf1 to Cf6. The amplified signal charges are sampled and held in the capacitors CL1 to CL6 by the SMPL signal based on a control from the imaging control unit 214. The signal charge of each of the capacitors CL1 to CL6 is outputted in order from the capacitors CL1, CL2, CL3, CL4, CL5, and CL6 in proportion as the analog shift resistors 110 are synchronized with the CLK signal based on a control from the imaging control unit 214, and are switched on in order. As a result, the signal charges accumulated in the conversion elements S1-1 to S1-6 of the first line are outputted in order as analog data by the analog multiplexer 13.

Similarly to the reading operation of the conversion elements S1-1 to S1-6 of the first line, the reading operations from the conversion elements S2-1 to S2-6 of the second line up to the conversion elements S6-1 to S6-6 of the sixth line are performed in order.

Incidentally, if the signal charges from each of the signal wires M1 to M6 are sample-held in the capacitors CL1 to CL6 by the SMPL signal at the reading time of the conversion elements of the first line, the capacitors Cf1 to Cf6 are reset by the RES signal, and after that, the drive signal can be applied to the drive wire G2. That is, during the signal charges from the conversion elements of the first line are subjected to series conversion operation by the analog multiplexer 13, the signal charges of the conversion elements S2-1 to S2-6 of the second line can be transferred at the same time. In this manner, the incident radiation is converted into a light of the wavelength region detectable by the conversion element by using the wavelength converter 142, and the light is converted into the electric charge by the conversion element, and the radiation information is read as the electrical signal, so that the image data of the subject can be obtained.

In the present embodiment, the reading mode by the signal processing circuit unit 102 includes three reading modes of a unit-pixel reading mode, four-pixel-addition reading mode, and nine-pixel-addition reading mode. Each reading mode by this signal processing circuit unit 102 is performed based on a control from the imaging control unit 214. The unit-pixel reading mode, as described in FIG. 3, is a mode for reading the signal charge from the conversion element for every one line by giving the drive signal from the drive circuit unit 101 to every one line in order.

Figure 4:
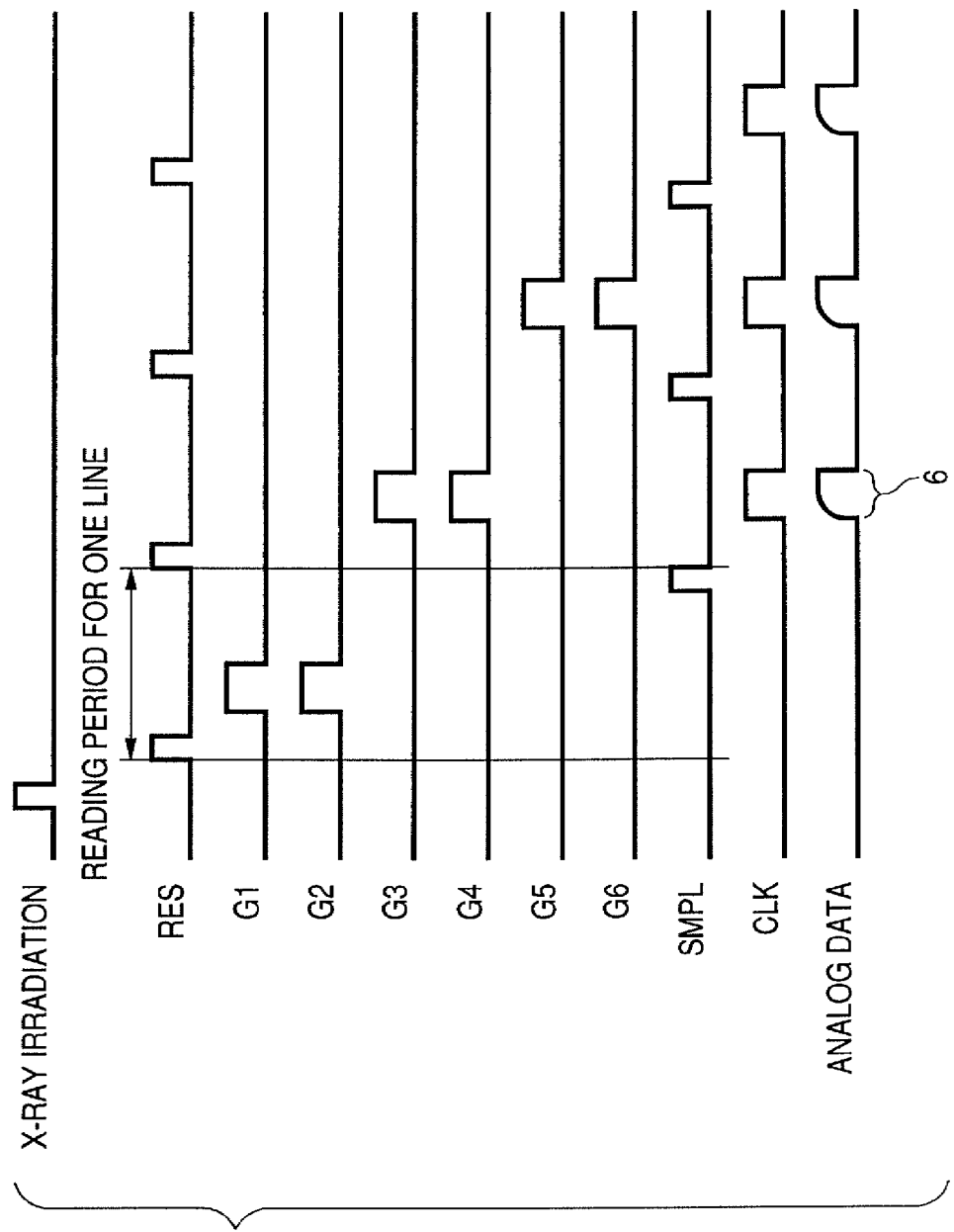
FIG. 4 is a timing chart illustrating a second method for driving (four-pixel-addition reading mode) the radiation imaging apparatus.

FIG. 4 is a timing chart illustrating a second method for driving (four-pixel-addition reading mode) of the radiation imaging apparatus 140.

The four-pixel-addition reading mode illustrated in FIG. 4 is a mode in which the signal charges in a total four unit-pixels of the unit-pixels of two rows by two columns are bound and these signals are read as the signal charge of one multi-pixel. In this case, in the present embodiment, by a control from the imaging control unit 214, the drive signals are given simultaneously to the drive wires of two lines from the drive circuit unit 101, and at the same time, in the signal processing circuit unit 102, the charge signals for two lines are simultaneously read. After reading, the addition (digital addition) of the electric charges for two lines are performed. In FIG. 4, the drive signals are given simultaneously to two lines each of each pair of drive wires G1 and G2, G3 and G4, and G5 and G6.

Figure 5:
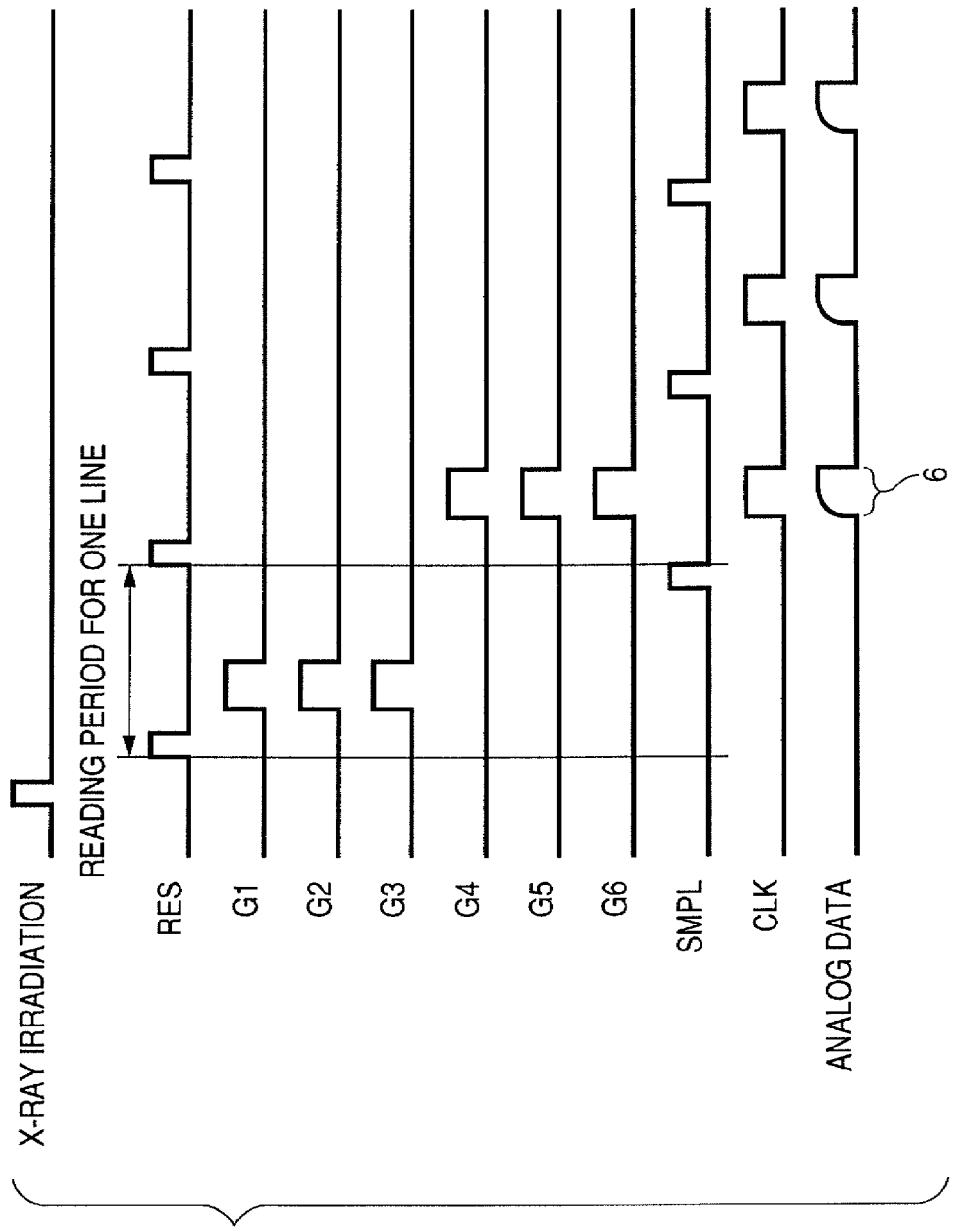
FIG. 5 is a timing chart illustrating a third method for driving (nine-pixel-addition reading mode) the radiation imaging apparatus.

FIG. 5 is a timing chart illustrating a third method for driving (nine-pixel-addition reading mode) of the radiation imaging apparatus 140.

The nine-pixel-addition reading mode illustrated in FIG. 5 is a mode in which the signal charges in a total nine unit-pixels of the unit-pixels of three rows by three columns are bound and these signals are read as the signal charge of one multi-pixel. In this case, in the present embodiment, by a control from the imaging control unit 214, the drive signals are given simultaneously to the drive wires of three lines from the drive circuit unit 101, and at the same time, in the signal processing circuit unit 102, the charge signals for three lines are simultaneously read. After reading, the addition of the charge signals for three lines are performed. In FIG. 5, the drive signals are given simultaneously to three lines each of each pair of drive wires G1, G2 and G3, and G4, G5 and G6.

As illustrated in FIGS. 4 and 5, by addition and reading the pixels, the reading time is shortened, and a frame rate is increased at the moving image radiographing time, and an S/N ratio is also improved.

Next, a method for extracting a defective pixel in the radiation imaging system of the present embodiment will be described. In the present embodiment, as described above, the radiographing by three reading modes described in FIGS. 3, 4, and 5 can be performed. In the radiation imaging system of the present embodiment, a defect coordinate table corresponding to each reading mode is, for example, stored in the external memory device 161, and when each reading mode is designated from the imaging control unit 214, the radiographed image data is corrected by using the corresponding defect coordinate table.

First, a production process of the defect coordinate table in the radiation imaging system of the present embodiment will be described.

Figure 6:
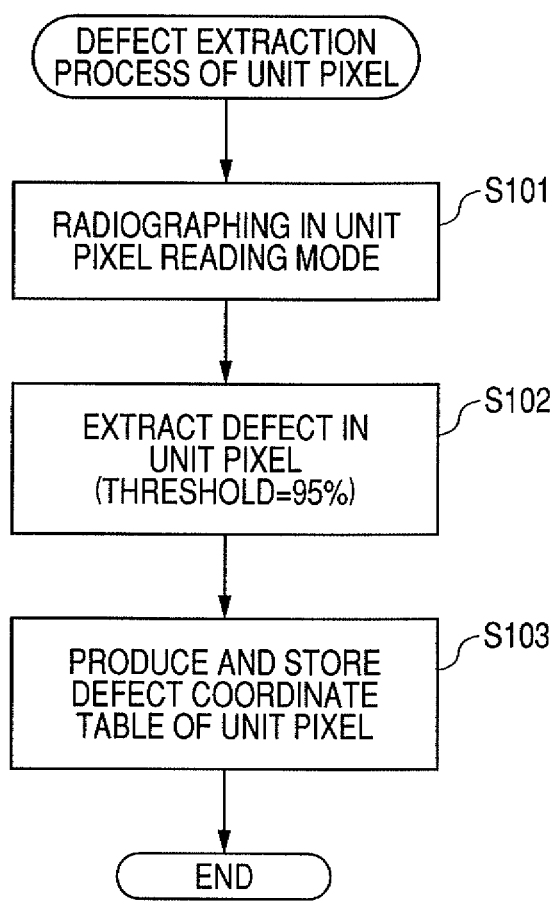
FIG. 6 is a flowchart illustrating a production process of a defect coordinate table used for a unit-pixel reading mode of FIG. 3.

FIG. 6 is a flowchart illustrating a production process of a defect coordinate table used for the unit-pixel reading mode of FIG. 3. First, at step S101, the imaging control unit 214, with the radiographing mode taken as a unit-pixel reading defect extracting mode, allows radiation to be generated from the radiation generating apparatus 120 in a state in which the subject 126 does not exist between the radiation generating apparatus 120 and the radiation imaging apparatus 140, and allows the radiation imaging apparatus 140 to perform radiographing. The imaging control unit 214 performs a control for transferring the analog data of each unit-pixel read from the radiation imaging apparatus 140 by the radiographing to the image processing unit 10.

Subsequently, at step S102, the imaging control unit 214, controls the image processing unit 10, and extracts the defect of the unit-pixel from within the radiographed image data. Specifically, this extraction processing of the defect of the unit-pixel compares the output value of each read unit-pixel and a certain threshold value (predetermined value), and extracts the unit-pixel whose output value is out of the threshold value as a defect. In the present embodiment, when the output value in the normal unit-pixel is taken as 100%, the threshold value of the output value is taken as 95%, and the unit-pixel whose output value is below 95% is extracted as a defect.

Subsequently, at step S103, the imaging control unit 214, based on the extraction result of the defect unit-pixel, produces a unit-pixel defect coordinate table including defect information (positional information indicating row and column and the like) regarding the defect unit-pixel, and this table is stored in the external memory device 161. By going through the processings of these steps S101 to S103, the defect information regarding the defect unit-pixel is stored in the external memory device 161.

Figure 7:
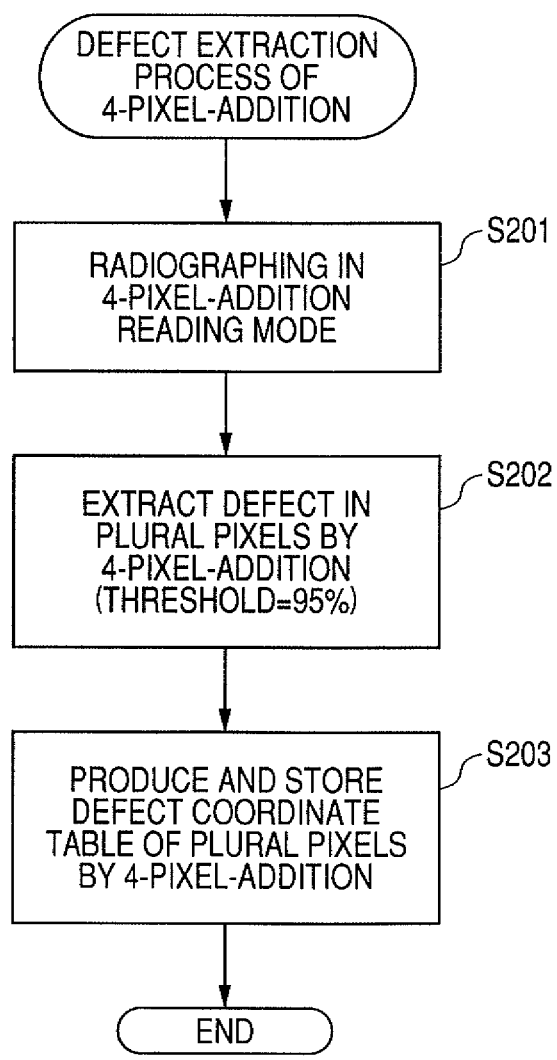
FIG. 7 is a flowchart illustrating the production process of the defect coordinate table used for a four-pixel-addition reading mode of FIG. 4.

FIG. 7 is a flowchart illustrating a production process of the defect coordinate table used for the four-pixel-addition reading mode of FIG. 4. First, at step S201, the imaging control unit 214, with the radiographing mode taken as the four-pixel-addition reading defect extracting mode, allows radiation to be generated from the radiation generating apparatus 120 in a state in which the subject 126 does not exist between the radiation generating apparatus 120 and the radiation imaging apparatus 140, and allows the radiation imaging apparatus 140 to perform radiographing. The imaging control unit 214 performs a control for transferring the analog data in the multi-pixel for the four unit-pixels read from the radiation imaging apparatus 140 by the radiographing to the image processing unit 10.

Subsequently, at step S202, the imaging control unit 214 controls the image processing unit 10 and extracts the defects of the multi-pixel from within the radiographed image data. Specifically, this extraction processing of the defects of the multi-pixel compares the output value of each of the read multi-pixel and a certain threshold value (predetermined value), and extracts the multi-pixel whose output value is out of the threshold value as defects. In the present embodiment, when the output value in the normal multi-pixel is taken as 100%, the threshold value of the output value is taken as 95%, and the multi-pixel whose output value is below 95% are extracted as the defects.

Subsequently, at step S203, the imaging control unit 214, based on the extraction result of the defective multi-pixel, produces a defect coordinate table of the multi-pixel by the four-pixel-addition including the defect information (positional information indicating row and column and the like) regarding the defective multi-pixel, and this table is stored in the external memory device 161. By going through the processings these steps S201 to S203, the defect information regarding the multi-pixel by the four-pixel-addition is stored in the external memory device 161.

Figure 8:
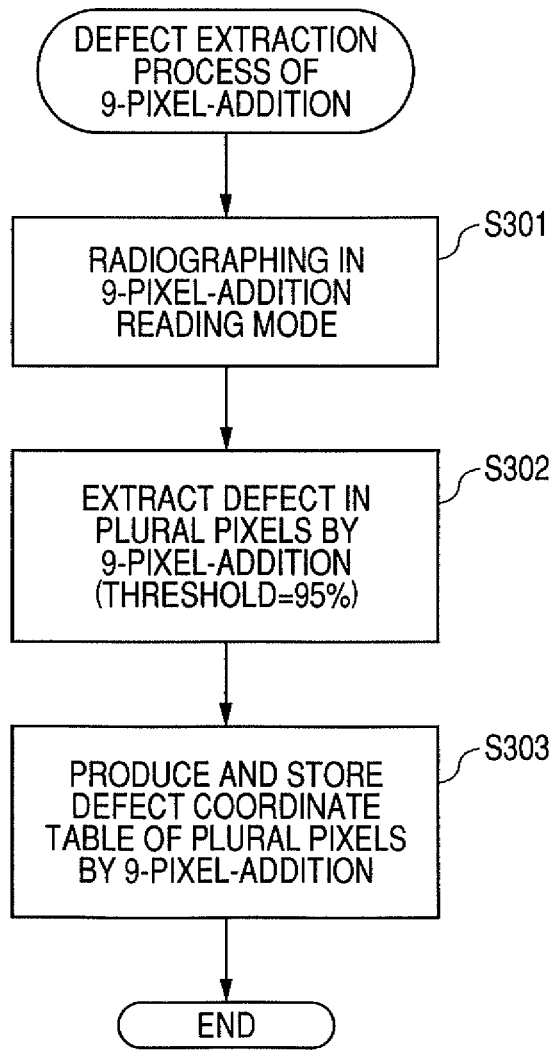
FIG. 8 is a flowchart illustrating the production process of the defect coordinate table used for a nine-pixel-addition reading mode of FIG. 5.

FIG. 8 is a flowchart illustrating the production process of the defect coordinate table used for the nine-pixel-addition reading mode of FIG. 5.

First, at step S301, the imaging control unit 214, with the radiographing mode taken as the nine-pixel-addition reading defect extracting mode, allows radiation to be generated from the radiation generating apparatus 120 in a state in which the subject 126 does not exist between the radiation generating apparatus 120 and the radiation imaging apparatus 140, and allows the radiation imaging apparatus 140 to perform radiographing. The imaging control unit 214 performs a control for transferring the analog data in the multi-pixel for the nine unit-pixels read from the radiation imaging apparatus 140 by the radiographing to the image processing unit 10.

Subsequently, at step S302, the imaging control unit 214 controls the image processing unit 10 and extracts the defects of the multi-pixel from within the radiographed image data. Specifically, this extraction processing of the defects of the multi-pixel compares the output value of each of the read multi-pixel and a certain threshold value (predetermined value), and extracts the multi-pixel whose output value is out of the threshold value as defects. In the present embodiment, when the output value in the normal multi-pixel is taken as 100%, the threshold value of the output value is taken as 95%, and the multi-pixel whose output value is below 95% are extracted as the defects.

Subsequently, at step S303, the imaging control unit 214, based on the extraction result of the defective multi-pixel, produces the multi-pixel defect coordinate table by the nine-pixel-addition including the defect information (positional information indicating row and column and the like) regarding the defective multi-pixel, and this table is stored in the external memory device 161. By going through the processings of these steps S301 to S303, the defect information regarding the multi-pixel by the nine-pixel-addition is stored in the external memory device 161.

Incidentally, the extraction processing of the defects illustrated in FIGS. 6 to 8, for example, may be performed at the factory shipment time of the radiation imaging apparatus 143. Further, the defect extracting mode is different from the normal radiographing mode, and it is a mode in which the output value of each read pixel and a certain threshold (predetermined value) are compared, and the pixel whose output value is out of the threshold value is extracted as a defect. That is, the defect extracting mode allows radiation from the radiation generating apparatus 120 to be irradiated on the photoelectric conversion circuit unit 143 in a state in which the subject 126 is not present between the radiation generating apparatus 120 and the radiation imaging apparatus 140, and reads the electric charge of each pixel, and loads it to the image processing unit 10 as an image data, and determines whether or not the each pixel is defective based on a certain threshold value. The pixel determined as defective has its positional information (information on row and column and the like) stored in the defect coordinate table.

Figures 9A, 9B:
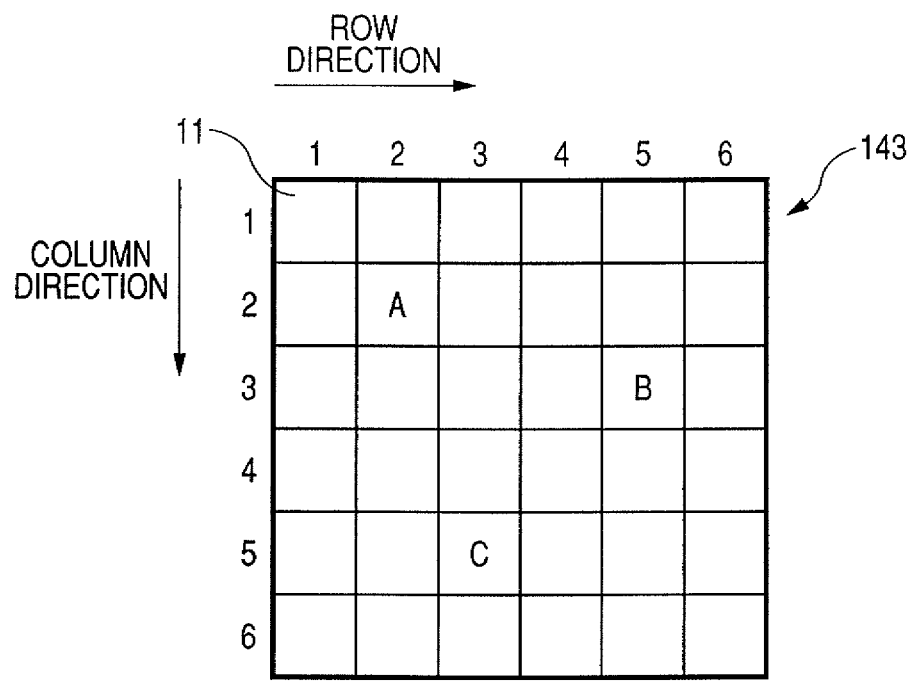
FIGS. 9A and 9B are views illustrating a defective unit-pixel when the radiation imaging apparatus of FIG. 2 is read by a unit-pixel reading mode and one example of a unit-pixel defect coordinate table.

FIGS. 9A and 9B are views illustrating the defect unit-pixel when the radiation imaging apparatus of FIG. 2 is read by the unit-pixel reading mode and one example of the unit-pixel defect coordinate table. Here, in FIG. 9A, the position of the defect unit-pixel when read by the unit-pixel reading mode is illustrated, and in FIG. 9B, one example of the unit-pixel defect coordinate table is illustrated. In the present example, as shown in FIGS. 9A and 9B, the defect unit-pixels as illustrated in A to C exist.

Figures 10A, 10B:
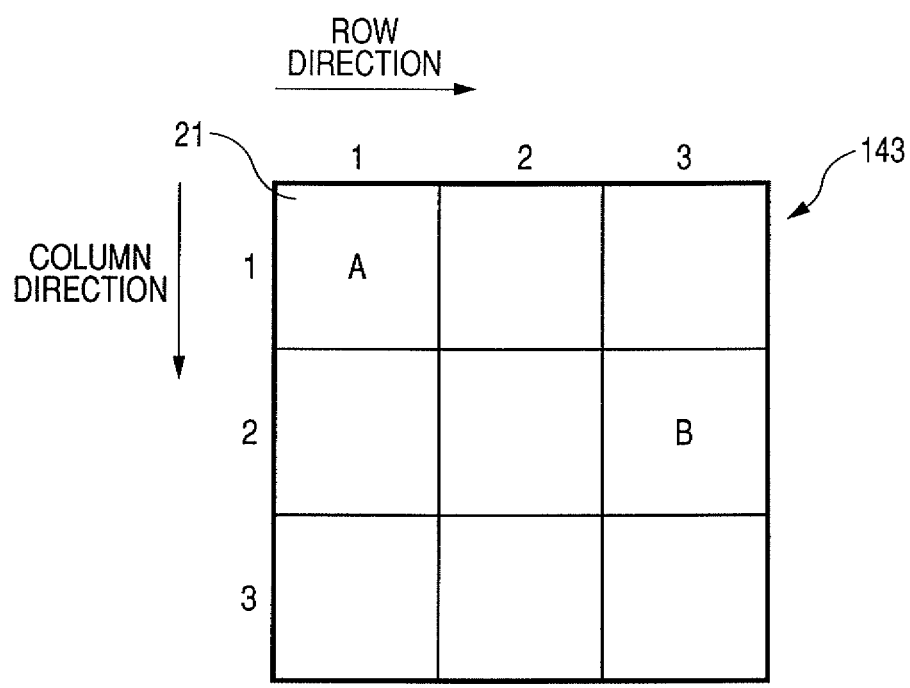
FIGS. 10A and 10B are views illustrating a defective multi-pixel when the radiation imaging apparatus of FIG. 2 is read by the four-pixel-addition reading mode and one example of a defect coordinate table of multi-pixels by the four-pixel-addition.

FIGS. 10A and 10B are views illustrating the defective multi-pixel when the radiation imaging apparatus of FIG. 2 is read by the four-pixel-addition reading mode and one example of the multi-pixel defect coordinate table by the four-pixel-addition. Here, in FIG. 10A, the positions of the defective multi-pixel when read by the four-pixel-addition reading mode are illustrated, and in FIG. 10B, one example of the coordinate table of the defective multi-pixel by the four-pixel-addition is illustrated. To perform the four-pixel-addition reading, as illustrated in FIG. 10A, the unit-pixel 11 of two rows by two columns is equivalent to one multi-pixel 21, and the image data outputted from the radiation imaging apparatus 140 becomes the data of a total of nine multi-pixel 21 of three rows by three columns. In the present example, as illustrated in FIGS. 10A and 10B, the defective multi-pixel 21 as illustrated in A and B exists.

FIGS. 11A and 11B are views illustrating the defective multi-pixel when the radiation imaging apparatus of FIG. 2 is read by the nine-pixel-addition reading mode and one example of the multi-pixel defect coordinate table by the nine-pixel-addition. Here, in FIG. 11A, the position of the defective multi-pixel when read by the nine-pixel-addition mode is illustrated, and in FIG. 11B, one example of the multi-pixel defect coordinate table by the nine-pixel-addition is illustrated. To perform the nine-pixel-addition reading, as illustrated in FIG. 11A, the unit-pixel 11 of three rows by three columns is equivalent to one multi-pixel 31, and the image data outputted from the radiation imaging apparatus 140 is the data of a total of four multi-pixel 31 of two rows by two columns. In the present example, as illustrated in FIGS. 11A and 11B, the defective multi-pixel 31 as illustrated by A exists.

As illustrated in FIGS. 9A to 11B, as the number of the pixel-addition increases, so the number of the defects decreases. This will be described below.

In the case of the four-pixel-addition reading mode illustrated in FIG. 10A, four unit-pixels 11 for two rows by two columns are read as one multi-pixel 21. Hence, the output value of the multi-pixel 21 becomes simply four times that of the unit-pixel 11. Further, an effect occupied by each unit-pixel 11 in one multi-pixel 21 is ¼ (25%). Similarly, in the case of the nine-pixel-addition reading mode illustrated in FIG. 11A, nine unit-pixels 11 for three rows by three columns are read as one multi-pixel 31, and therefore, the output value of the multi-pixel 31 becomes simply nine times that of the unit-pixel 11. Further, an effect occupied by each unit-pixel 11 in one multi-pixel 31 is ⅑ (11%).

In this manner, in the pixel-addition reading, as the number of the pixel-addition increases, so a ratio occupied by the effect of each unit-pixel 11 decreases, and an effect of the defect of the unit-pixel 11 is hard to be received. Hence, depending on the defect of the unit-pixel, there are often the cases where such defect is no longer the defect as the multi-pixel by performing the pixel-addition reading. Thus, in the present embodiment, the defect coordinate table for performing the correction of the defect of the pixel is also prepared for each pixel-addition mode, and is stored, and when radiographing the subject, the correction of the defect of the pixel is performed by referring to the defect coordinate table corresponding to each pixel-addition reading mode.

In the present embodiment, the threshold value when extracting the defect is taken as a pixel whose output value is reduced not less than 5% for average of the entire surface, in other words, whose output value is below 95% for average of the entire surface.

As illustrated in FIGS. 9A and 9B, in case of reading by the unit-pixel reading mode, the defective unit-pixel exists in a total of three pieces of A to C. As against the output value of the normal unit-pixel, the output value of the unit-pixel A is 50% (reduced by 50%), the output value of the unit-pixel B is 70% (reduced by 30%), and the output value of the unit-pixel C is 90% (reduced by 10%), and each output value is far below the threshold value, and therefore, each unit-pixel is extracted as the defective unit-pixel. The defect information regarding these defective unit-pixels A to C is registered in the unit-pixel defect coordinate table of FIG. 9B. Here, in the present embodiment, the unit-pixel other than the defective unit-pixels A to C is taken as a normal pixel and its output value is taken as an average (reduced by 0%).

As illustrated in FIGS. 10A and 10B, in a case of reading by the four-pixel-addition reading mode, the defective multi-pixels exist in a total of two pieces of A and B. The detective unit-pixel C illustrated in FIGS. 9A and 9B has 90% (reduced by 10%) of the output value in the unit-pixel reading mode, and is defective. In the four-pixel-addition reading mode, since the reduction in the output value in the other three unit-pixels except for the defective unit-pixel C is 0%, the output value of the multi-pixel 21 including this defective unit-pixel C is 90%+100%+100%+100%=390%. In the case of the four-pixel-addition reading, as compared with the unit-pixel reading, the output value is a normal value of 400% which is 4 times that of the unit-pixel reading, and the output value of the multi-pixel 21 including the defective unit-pixel C is an output value of 390%/400%=97% as against the output value of the normal multi-pixel 21. Hence, this value satisfies a value within 5% which is the threshold value of the defect extraction, and therefore, the multi-pixel 21 including the defective unit-pixel C is not defective in the four-pixel-addition reading mode.

On the other hand, the multi-pixel 21 (multi-pixel A) including a defective unit-pixel A of FIGS. 9A and 9B becomes an output value of 50%+100%+100%+100%=350%, and becomes an output value of 350%/400%=87% as against the normal multi-pixel 21, and therefore, does not come within 5% of the threshold value, and is extracted as defective. Further, the multi-pixel 21 (multi-pixel B) including the defective unit-pixel B of FIGS. 9A and 9B becomes the output value of 70%+100%+100%+100%=370%, and becomes the output value of 370%/400%=92% as against the normal multi-pixel 21, and therefore, it does not come within 5% of the threshold value, and is extracted as defective. The defective information regarding these defective multi-pixel A and B is registered in the multi-pixel defect coordinate table by the four-pixel-addition reading of FIG. 10B. In this manner, the number of defects of the four-pixel-addition reading mode is a total of two pieces, and this is short of one piece when compared with the unit-pixel reading mode.

Similarly, as illustrated in FIGS. 11A and 11B, in a case of reading by the nine-pixel-addition reading mode, the multi-pixel 31 (multi-pixel A) including the defective unit-pixel A of FIGS. 9A and 9B becomes the output value of 50%+100%×8=850%. Since this multi-pixel A becomes the output value of 850%/900%=94% as against the normal multi-pixel 31, it does not come within 5% of the threshold value, and is extracted as defective. Further, the multi-pixel 31 including the defective unit-pixel B of FIGS. 9A and 9B becomes the output value of 70%+100%×8=870%, and becomes the output value of 870%/900%=96% as against the normal multi-pixel 31, and therefore, comes within 5% of the threshold value, and does not become defective. Further, the multi-pixel 31 including the defective unit-pixel C of FIGS. 9A and 9B becomes the output value of 90%+100%×8=890%, and becomes the output value of 890%/900%=98% as against the normal multi-pixel 31, and therefore, it comes within 5% of the threshold value, and does not become defective. As a result, in the nine-pixel-addition reading mode, the multi-pixel A only is registered in the multi-pixel defect coordinate table by the nine-pixel-addition as defective.

In this manner, in the present embodiment, the defect coordinate table is prepared in three types and is stored according to the reading mode of the pixel, and at the time of radiographing the object, the defect coordinate table corresponding to the reading mode of each pixel is referred to, and the defect correction of the image data is performed. By preparing the defect coordinate table for each pixel reading mode in this manner, the number of defects can be reduced at the pixel-addition time.

Next, a method for correction processing of the defective pixel in the radiation imaging system of the present embodiment will be described.

Figure 12:
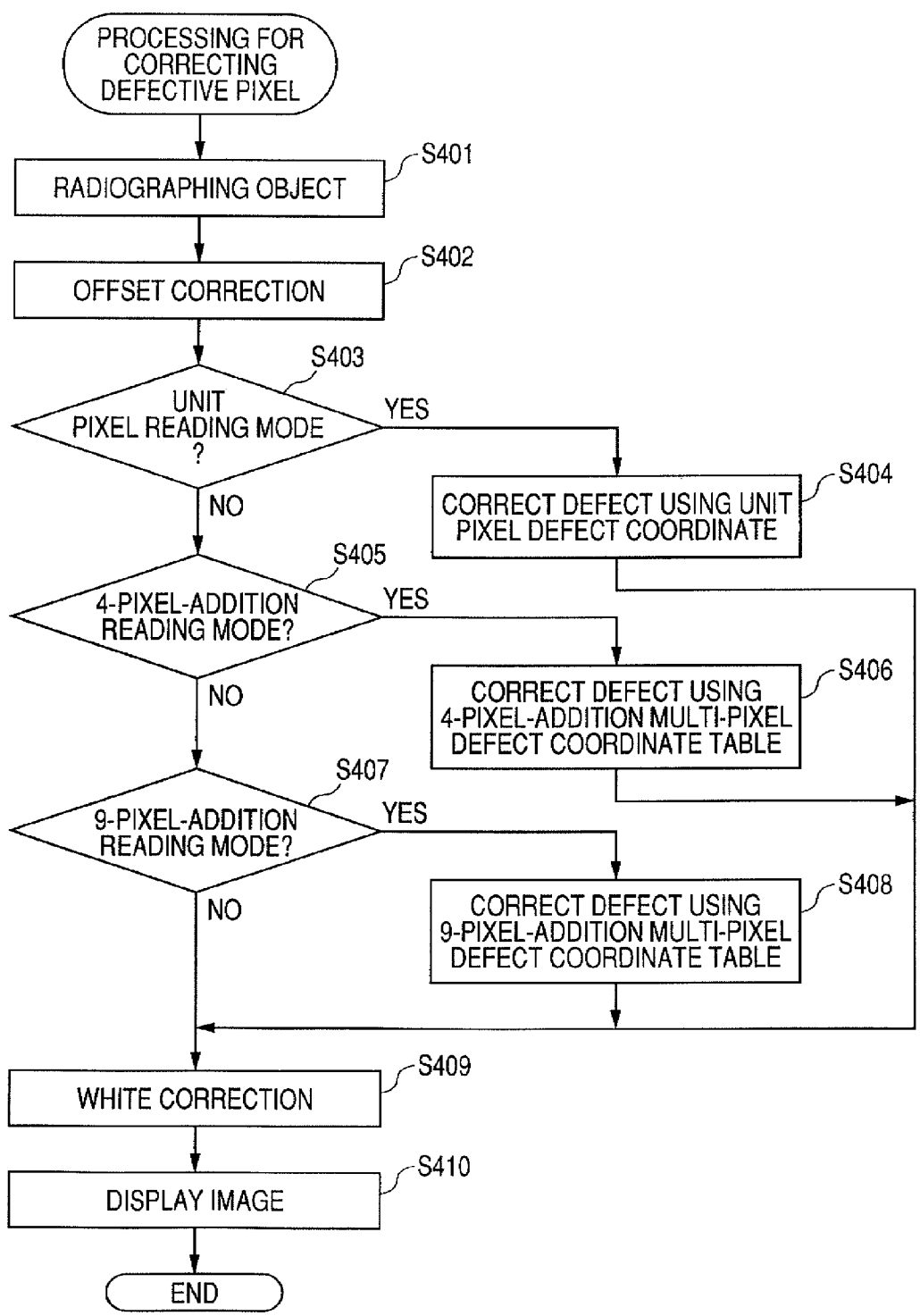
FIG. 12 is a flowchart illustrating the correction processing of the defective pixel in the radiation imaging system according to the first embodiment.

FIG. 12 is a flowchart illustrating the correction processing of the defective pixel in the radiation imaging system according to the first embodiment. When a radiographing mode (pixel reading mode) is selected by an operator 305, the system control unit 310 instructs a radiographing condition based on the selected radiographing mode for the imaging control unit 214, and the imaging control unit 214 performs the radiographing of the object based on the radiographing condition (step S401).

After completing the radiographing, at step S402, the imaging control unit 214 controls the image processing unit 10 and performs an offset correction of the image data radiographed by the radiation imaging apparatus 140.

Subsequently, at step S403, the imaging control unit 214 determines whether or not the radiographing mode (pixel reading mode) selected at step S401 is the unit-pixel reading mode. As a result of this determination, when the selected radiographing mode is a unit-pixel reading mode, the procedure advances to step S404. Then, at step S404, the imaging control unit 214 controls the image processing unit 10 and performs the defect correction of the image data radiographed by the radiation imaging apparatus 140 by using the unit-pixel defect coordinate table stored in the external memory device 161. On the other hand, as a result of the determination at step S403, when the selected radiographing mode is not the unit-pixel reading mode, the procedure advances to step S405.

Subsequently, at step S405, the imaging control unit 214 determines whether or not the radiographing mode (pixel reading mode) selected at step S401 is the four-pixel-addition reading mode. As a result of this determination, when the selected radiographing mode is the four-pixel-addition reading mode, the procedure advances to step S406. Then, at step S406, the imaging control unit 214 controls the image processing unit 10 and performs the defect correction of the image data radiographed by the radiation imaging apparatus 140 by using the multi-pixel defect coordinate table by the four-pixel-addition stored in the external memory device 161. On the other hand, as a result of the determination at step S405, when the selected radiographing mode is not the four-pixel-addition reading mode, the procedure advances to step S407.

Subsequently, at step S407, the imaging control unit 214 determines whether or not the radiographing mode (pixel reading mode) selected at step S401 is the nine-pixel-addition reading mode. As a result of this determination, when the selected radiographing mode is the nine-pixel-addition reading mode, the procedure advances to step S408. Then, at step S408, the imaging control unit 214 controls the image processing unit 10 and performs the defect correction of the image data radiographed by the radiation imaging apparatus 140 by using the multi-pixel defect coordinate table by the nine-pixel-addition stored in the external memory device 161. On the other hand, as a result of the determination at step S407, when the selected radiographing mode is not the nine-pixel-addition reading mode, the procedure advances to step S409.

When the processings of steps S404, S406, and S408 are completed or at step S407, when it is determined that the selected radiographing mode is not the nine-pixel-biding reading mode, subsequently, at step S409, the imaging control unit 214 controls the image processing unit 10 and performs a white correction for the image data.

Subsequently, at step S410, the image data processed at the image processing unit 10 is displayed at the display unit 160 as an image.

By going through the processings of the above described steps S401 to S410, the correction processing of the defective pixel of the image data radiographed by the radiation imaging apparatus 140 is performed.

Here, in the present embodiment, though the image processing unit 10 is disposed separately from the radiation imaging apparatus 140, the present invention is not limited to this, the image processing unit 10 may be disposed within the radiation imaging apparatus 140. Further, in the present embodiment, though the defect coordinate table corresponding to respective pixel reading modes is stored in the external memory device 161, the present invention is not limited to this, and each defect coordinate table may be stored in storage means provided within the radiation imaging apparatus 140. Further, the image processing unit 10 and the storage means having the defect coordinate table may be provided within the radiation imaging apparatus 140, and the image processing such as the offset correction, white correction, and defect correction may be performed within the radiation imaging apparatus 140.

Further, in the present embodiment, though a description has been made on the pixel-addition reading mode by taking the four-pixel-addition reading mode and the nine-pixel-addition reading mode as the examples, the present invention is not limited to this, and any other addition reading mode can be also applied to the invention.

Second Embodiment

Next, a second embodiment of the present invention will be described. Since the configuration of a radiation imaging system according to the second embodiment is the same as the configuration of the radiation imaging system according to the first embodiment illustrated in FIG. 1, the description thereof will be omitted. The radiation imaging system according to the second embodiment is different in a method for extracting a defective pixel as against the radiation imaging system according to the first embodiment, and therefore, the description on the method alone will be made. At this time, in the second embodiment, a description will be made by an example in which the photoelectric conversion circuit unit 143 illustrated in FIG. 2 comprises a total of 64 pieces of eight by eight pixels of the unit-pixel.

Figure 13:
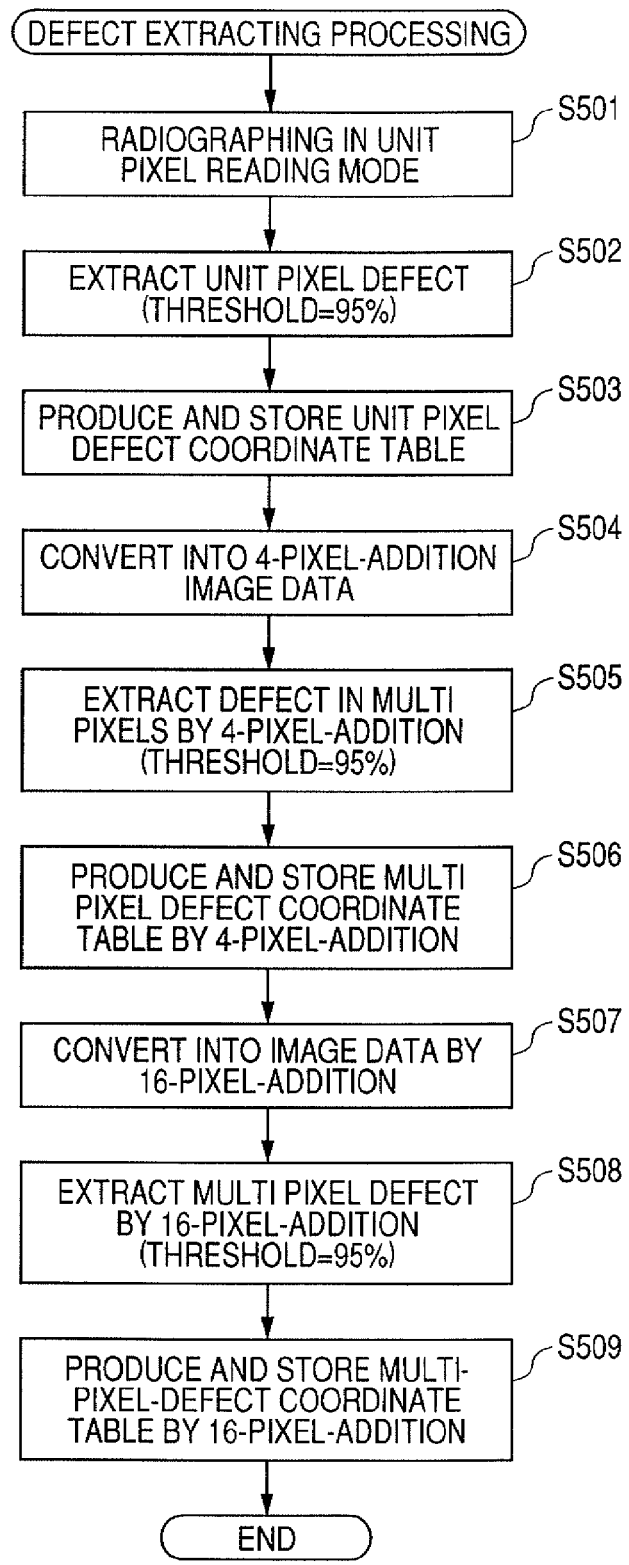
FIG. 13 is a flowchart illustrating a method for extracting the defective pixel in the radiation imaging system according to a second embodiment.

FIG. 13 is a flowchart illustrating a method for extracting a defective pixel in the radiation imaging system according to the second embodiment.

In the first embodiment, though the radiographing is performed by the defect extracting mode for each pixel reading method, in the second embodiment, the radiographing only of a defect extracting mode by unit-pixel reading is performed. Specifically, the radiographing by the defect extracting mode by the unit-pixel reading is performed, and four-pixel-addition and 16-pixel-addition are performed for the data (output value) of each unit-pixel, and the defect extracting in each multi-pixel when performing the reading by each pixel-addition reading mode is performed. This is a processing equivalent to (convert into image data by four-pixel-addition) and (convert into image data by 16-pixel-addition) of the flowchart illustrated in FIG. 13.

First, at step S501, the imaging control unit 214 takes a radiographing mode as a unit-pixel reading defect extracting mode, and allows radiation to be generated from a radiation generating apparatus 120 in a state in which no subject 126 exists between the radiation generating apparatus 120 and a radiation imaging apparatus 140, and allows the radiation imaging apparatus 140 to perform radiographing. The imaging control unit 214 performs a control for transferring the analog data of each unit-pixel read from the radiation imaging apparatus 140 by the radiographing to an image processing unit 10.

Subsequently, at step S502, the imaging control unit 214 controls the image processing unit 10 and extracts the defect of the unit-pixel from within the radiographed image data. Specifically, this extracting processing of the unit-pixel defect compares the output value of each read unit-pixel and a certain threshold value (predetermined value), and extracts the unit-pixel whose output value is out of the threshold value as a defect. In the present embodiment, when the output value in the normal unit-pixel is taken as 100%, the threshold value of the output value is taken as 95%, and the unit-pixel whose output value is below 95% is extracted as a defect. At this time, for example, the output value of each unit-pixel is stored in the memory within the image processing unit 10.

Subsequently, at step S503, the imaging control unit 214, based on the extraction result of the defective unit-pixel, produces the unit-pixel defect coordinate table including defect information (positional information indicating row and column and the like) regarding the defective unit-pixel, and this table is stored in an external memory device 161.

Subsequently, at step S504, by arithmetically processing the output value of each unit-pixel stored in the memory within the image processing unit 10, the output value is converted into the image data when performing the four-pixel-addition reading. The image data at this time is a data taking unit-pixels 11 of two rows by two columns as one multi-pixel.

Subsequently, at step S505, the imaging control unit 214 controls the image processing unit 10, and extracts the defect of the multi-pixel from within the image data converted at step S504. Specifically, the extracting processing of this multi-pixel defect compares the output value of each multi-pixel and a certain threshold value (predetermined value), and extracts the multi-pixel whose output value is out of the threshold value as a defect. In the present embodiment, when the output value in the normal multi-pixel is taken as 100%, the threshold value of the output value is taken as 95%, and the multi-pixel whose output value is below 95% is extracted as a defect.

Subsequently, at step S506, the imaging control unit 214, based on the extraction result of the defective multi-pixel at step S505, produces a multi-pixel defect coordinate table by the four-pixel-addition including the defect information regarding the defective multi-pixel and this table is stored in the external memory device 161.

Subsequently, at step S507, by arithmetically processing the output value of each unit-pixel stored in the memory within the image processing unit 10, this output value is converted into the image data when performing the 16-pixeladdition reading. The image data at this time is a data taking the unit-pixels 11 of four rows by four columns as one multi-pixel.

Subsequently, at step S508, the imaging control unit 214 controls the image processing unit 10, and extracts the defect of the multi-pixel from within the image data converted at step S507. Specifically, the extracting processing of this multi-pixel defect compares the output value of each multi-pixel and a certain threshold value (predetermined value), and extracts the multi-pixel whose output value is out of the threshold value as a defect. In the present embodiment, when the output value in the normal multi-pixel is taken as 100%, the threshold value of the output value is taken as 95%, and the multi-pixel whose output value is below 95% is extracted as a defect.

Subsequently, at step S509, the imaging control unit 214, based on the extraction result of the defective multi-pixel at step S508, produces a multi-pixel defect coordinate table by the 16-pixel-addition including the defect information regarding the defective multi-pixel and this table is stored in the external memory device 161.

By going through the processings of the above described steps S501 to S509, one time radiographing by the defect extracting mode by the unit-pixel reading can produce the pixel defect coordinate table by each reading mode (unit-pixel, four-pixel-addition, and 16-pixel-addition).

In the second embodiment, since the radiographing by the defect extracting mode in the unit-pixel reading is performed one time only, an advantage is afforded in that the work load of an operator 305 performing the radiographing can be reduced as compared with the first embodiment.

Figures 14A, 14B:
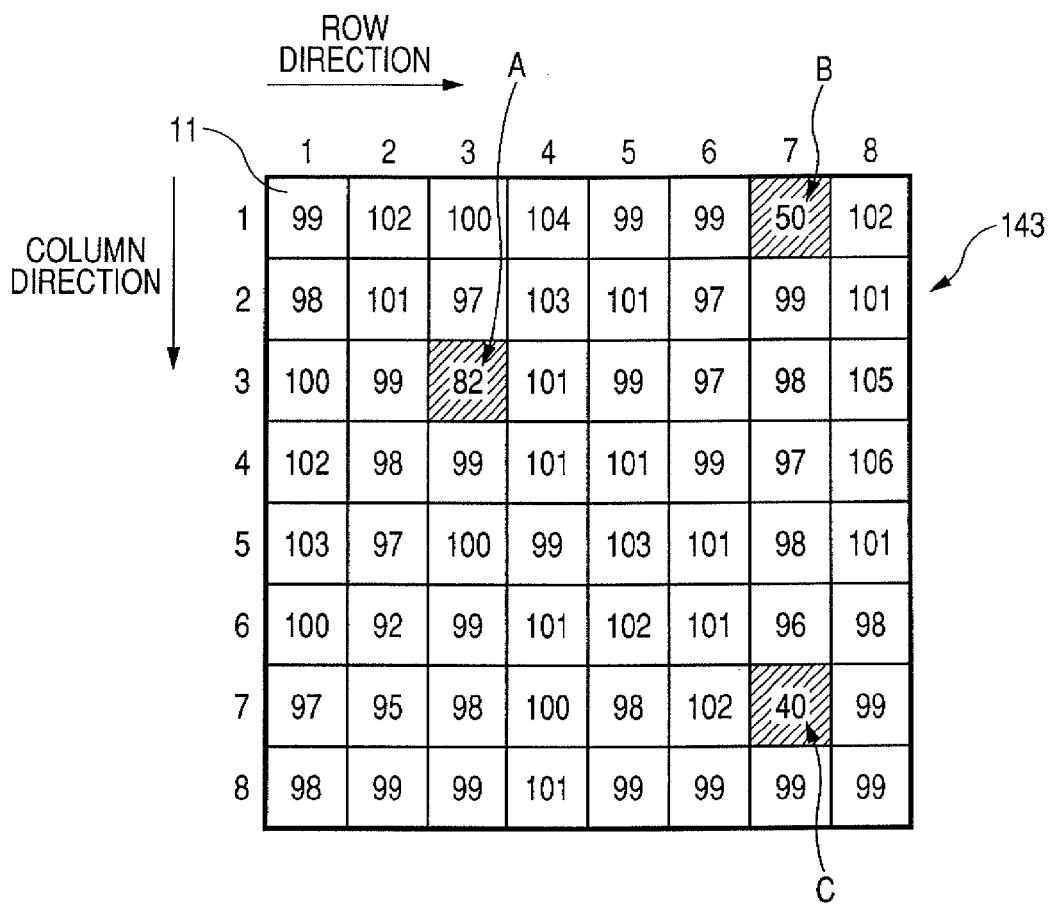
FIGS. 14A and 14B are views illustrating an output value in each unit-pixel and one example of the unit-pixel defect coordinate table.

FIGS. 14A and 14B are views illustrating the output value in each unit-pixel 11 and one example of the unit-pixel defect coordinate table. Here, in FIG. 14A, the output value in each unit-pixel 11 and the position of the defective pixel are illustrated, and in FIG. 14B, one example of the unit-pixel defect coordinate table is illustrated. In the present embodiment, as illustrated in FIGS. 14A and 14B, the defect unit-pixels as illustrated in A to C exist.

Figures 15A, 15B:
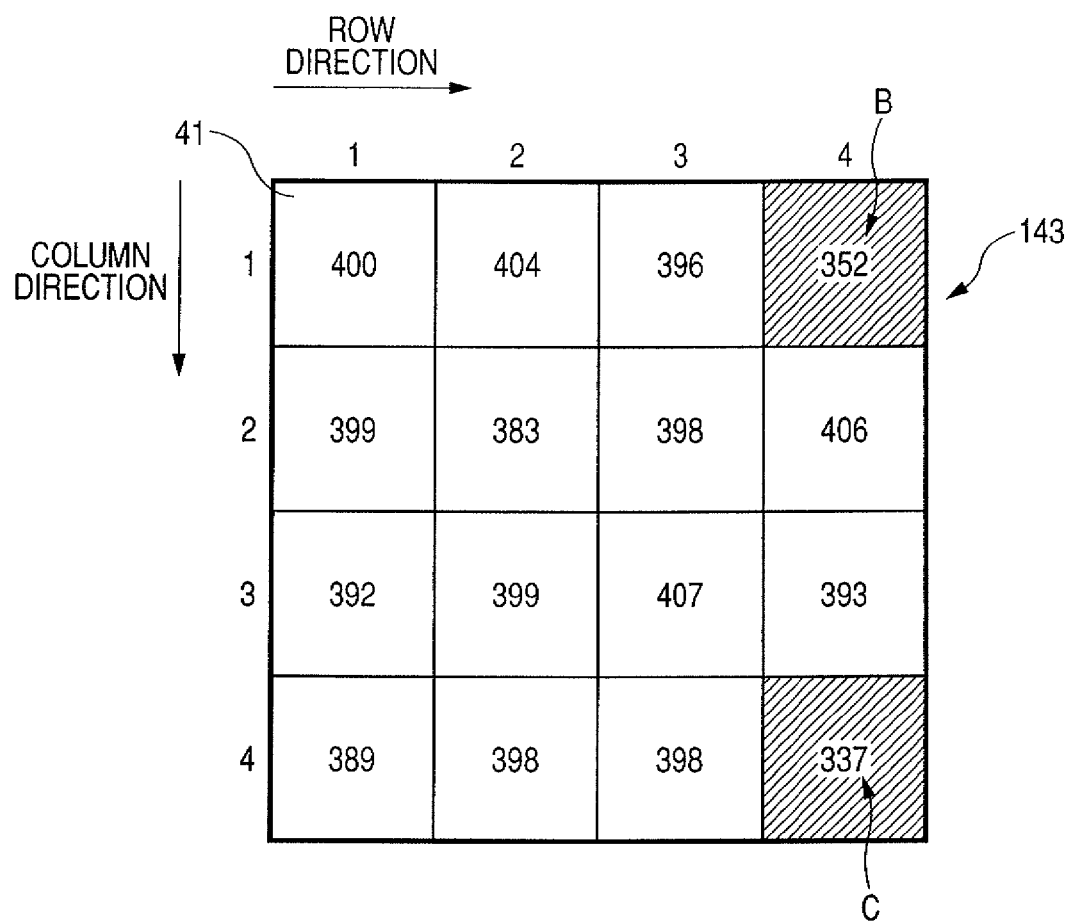
FIGS. 15A and 15B are views illustrating the output value of each of the multi-pixel by the four-pixel-addition and one example of the multi-pixel defect coordinate table by the four-pixel-addition.

FIGS. 15A and 15B are views illustrating the output value of each multi-pixel 41 by the four-pixel-addition and one example of the multi-pixel defect coordinate table by the four-pixel-addition. Here, in FIG. 15A, the output value in each multi-pixel 41 by the four-pixel-addition and the position of the defective pixel are illustrated, and in FIG. 15B, one example of the multi-pixel defect coordinate table by the four-pixel-addition is illustrated. To perform the four-pixel-addition, as illustrated in FIG. 15A, the unit-pixels 11 of two rows by two columns are equivalent to one multi-pixel 41, and the image data becomes a data of a total 16 pieces of multi-pixels 41 of four rows by four columns. In the present example, as illustrated in FIGS. 15A and 15B, the defective multi-pixel 41 illustrated in B and C exists.

Figures 16A, 16B:
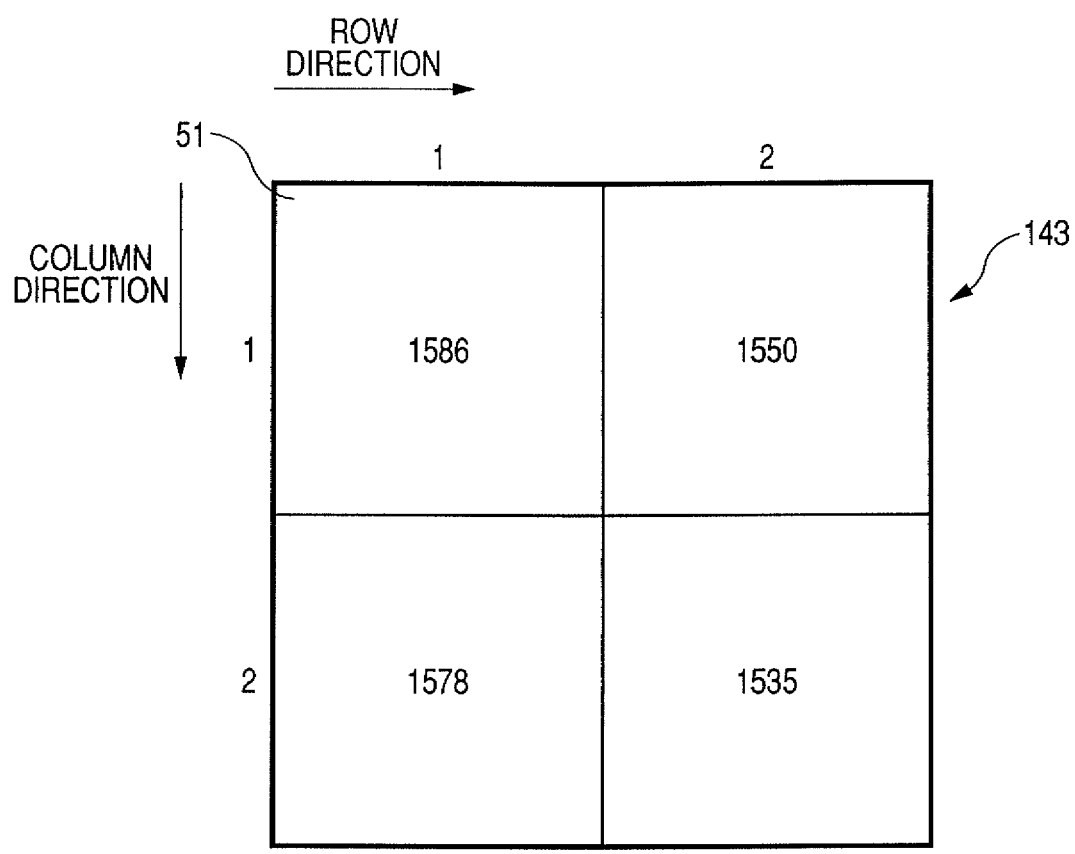
FIGS. 16A and 16B are views illustrating the output value of each of the multi-pixels in a 16-pixel-addition and one example of the multi-pixel defect coordinate table by the 16-pixel-addition.

FIGS. 16A and 16B are views illustrating the output value of each multi-pixel 51 by 16-pixel-addition and one example of the multi-pixel defect coordinate table by the 16-pixel-addition. Here, in FIG. 16A, the output value in each multi-pixel 51 by the 16-pixel-addition and the position of the defective pixel are illustrated, and in FIG. 16B, one example of the multi-pixel defect coordinate table by the 16-pixel-addition is illustrated. To perform the 16-pixel-addition, as illustrated in FIG. 16A, the unit-pixels 11 of four rows by four columns are equivalent to one multi-pixel 51, and the image data becomes a data of the multi-pixels 51 of a total four pieces of two rows by two columns. In the present example, as illustrated in FIGS. 16A and 16B, there exists no defective multi-pixel.

FIG. 15A is a view for addition the output values of the unit-pixels 11 of two rows by two columns of FIG. 14A, and FIG. 16A is a view for addition the output values of the unit-pixels 11 of four rows by four columns of FIG. 14A. The threshold value of the defective pixel in the second embodiment is a pixel of the output value below 95% as against the output value of the normal pixel.

In the unit-pixel reading mode, though the three defect unit-pixels 11 of A to C exist, at the four-pixel-addition time, the multi-pixel 41 including this defective unit-pixel A becomes non-defective by the four-pixel-addition due to the effect of the peripheral pixel, and therefore, it is excluded from the defective pixel. Here, at the four-pixel-addition time, the output value 100×4=400 is an average and the output value 400×0.95=380 becomes a threshold value of the defective pixel. Further, in the 16-pixel-addition, the multi-pixel 51 including the defective unit-pixel B and the multi-pixel 51 including the defective unit-pixel C are also non-defective, and the defect becomes zero. Here, at the 16-pixel-addition time, the output value 100×16=1600 is an average and the output value 1600×0.95=1520 becomes a threshold value of the defective pixel.

By providing the defect coordinate table for each pixel-addition mode in this manner, the number of defective pixel data is reduced, and the deterioration of the image quality can be reduced.

Further, in the present embodiment, though a description has been made on the pixel-addition reading mode by taking the four-pixel-addition reading mode and the 16-pixel-addition reading mode as the example, the present invention is not limited to this, and any other addition reading mode can be also applied to the invention.

Third Embodiment

Next, a third embodiment of the present invention will be described. Since the configuration of a radiation imaging system according to the third embodiment is the same as the configuration of the radiation imaging system according to the second embodiment, the description thereof will be omitted. The radiation imaging system according to the third embodiment is different from the radiation imaging system according to the second embodiment in that a method for extracting a defective pixel is different, and therefore, a description will be made only on that method.

Figure 17:
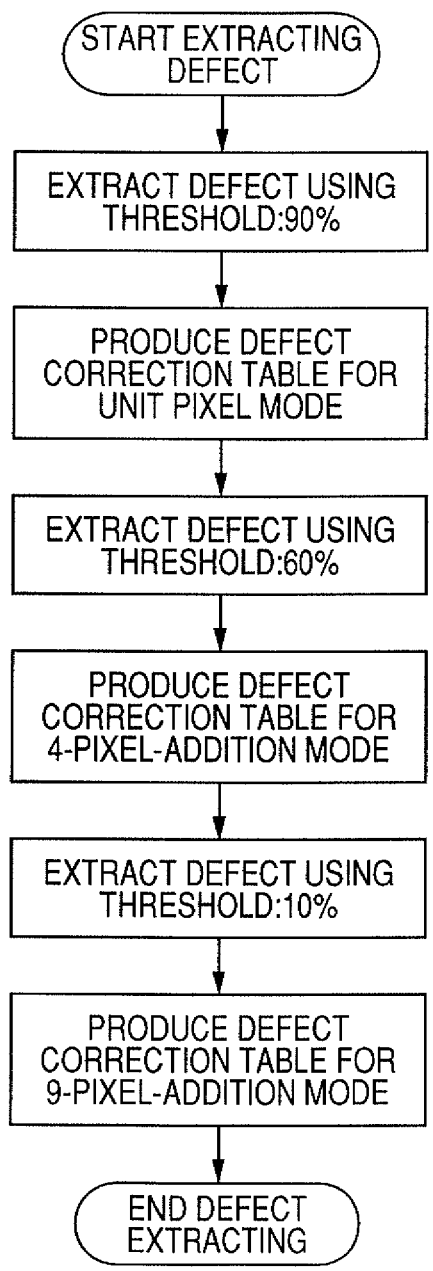
FIG. 17 is a flowchart illustrating the correction processing of the defective pixel in the radiation imaging system according to a third embodiment.

FIG. 17 is a flowchart illustrating a method for extracting a defective pixel in the radiation imaging system according to the third embodiment.

In the second embodiment, the radiographing of a defect extracting by unit-pixel reading is performed, and by the image processing, images by four-pixel-addition and nine-pixel-addition are produced, thereby performing the extracting of the defect. On the other hand, in the third embodiment, a threshold value is changed from the image by the unit-pixel reading, and the extraction of defect of each pixel-addition mode is performed.

First, the imaging control unit 214, with the radiographing mode taken as a unit-pixel reading defect extracting mode, allows radiation to be generated from a radiation generating apparatus 120 in a state in which no subject 126 exists between the radiation generating apparatus 120 and a radiation imaging apparatus 140, and allows the radiation imaging apparatus 140 to perform the radiographing. The imaging control unit 214 performs a control for transferring the analog data of each unit-pixel read from the radiation imaging apparatus 140 by the radiographing to an image processing unit 10.

Subsequently, the imaging control unit 214 controls an image processing unit 10, and extracts the defect of a unit-pixel from within the radiophotographed image data. Specifically, the extracting processing of this unit-pixel defect compares the output value of each read unit-pixel and a certain threshold value (predetermined value), and extracts the unit-pixel whose output value is out of the threshold value as a defect. In the present embodiment, when the output value in the normal unit-pixel is taken as 100%, the threshold value of the output value is taken as 90%, and the unit-pixel whose output value is below 90% is extracted as a defect. At this time, for example, the output value of each unit-pixel is stored in a memory within the image processing unit 10.

Subsequently, the imaging control unit 214, based on the extraction result of the defective unit-pixel, produces a unit-pixel defect coordinate table including defect information (positional information indicating row and column and the like) regarding the defective unit-pixel, and this table is stored in an external memory device 161.

Subsequently, the imaging control unit 214 controls the image processing unit 10, and extracts a four-pixel-addition defect from within the radiophotographed image data. Specifically, the extracting processing of this four-pixel-addition defect compares the output value of each read unit-pixel and a certain threshold value (predetermined value), and extracts the unit-pixel whose output value is out of the threshold value as a defect. In the present embodiment, when the output value in the normal unit-pixel is taken as 100%, the threshold value of the output value is taken as 60%, and the unit-pixel whose output value is below 60% is extracted as a defect. At this time, for example, the output value of each unit-pixel is stored in a memory within the image processing unit 10.

Subsequently, the imaging control unit 214, based on the extraction result of the defective unit-pixel, produces a four-pixel-addition defect coordinate table including defect information (positional information indicating row and column and the like) regarding the defective unit-pixel, and this table is stored in the external memory device 161.

Subsequently, the imaging control unit 214 controls the image processing unit 10, and extracts a nine-pixel-addition defect from within the radiophotographed image data. Specifically, the extracting processing of this nine-pixel-addition defect compares the output value of each read unit-pixel and a certain threshold value (predetermined value), and extracts the unit-pixel whose output value is out of the threshold value as a defect. In the present embodiment, when the output value in the normal unit-pixel is taken as 100%, the threshold value of the output value is taken as 10%, and the unit-pixel whose output value is below 10% is extracted as a defect. At this time, for example, the output value of each unit-pixel is stored in the memory within the image processing unit 10.

Subsequently, the imaging control unit 214, based on the extraction result of the defective unit-pixel, produces a nine-pixel defect coordinate table including defect information (positional information indicating row and column and the like) regarding the defective unit-pixel, and this table is stored in the external memory device 161.

By going through the above described steps, one time radiographing by the defect extracting mode by the unit-pixel reading can produce a pixel defect coordinate table by each reading mode (unit-pixel, four-pixel-addition, and nine-pixel-addition).

In the third embodiment, since the radiographing by the defect extracting mode in the unit-pixel reading is performed one time only, an advantage is afforded in that the work load of an operator 305 performing the radiographing can be reduced as compared with the first embodiment. Further, as compared with the second embodiment, since there is no need to generate the pixel-addition image, the processing can be made simple.

Further, in the third embodiment, as the pixel-addition increases, so the effect of the unit-pixel to the multi-pixel decreases, and therefore, the threshold value is changed for each pixel-addition mode, and the defect is extracted. For example, in the four-pixel-addition, an occupied ratio of the multi-pixel to the output value of the unit-pixel becomes one fourth. Hence, the threshold value can be made four times larger than the defect of the unit-pixel mode. For example, in the unit-pixel mode, though the pixel (threshold value 90%) whose output is reduced by 10% than the normal pixel is taken as a defect, in the four-pixel-addition, the pixel (threshold value 60%) whose output is reduced by 40% than the normal pixel can be taken as a defect. Further, in the nine-pixel-addition, a ratio occupied by the unit-pixel becomes one ninth, and therefore, the pixel (threshold value 10%) whose output is reduced by 90% is taken as a defect.

Further, in the third embodiment, though a description has been made on the pixel-addition reading mode by taking the four-pixel-addition reading mode and the nine-pixel-addition reading mode as the example, the present invention is not limited to this, and any other addition reading mode can be also applied to the invention.

According to the first to third embodiments of the present invention, since the defect information corresponding to the method for reading the pixel in the conversion unit is stored, by using the defect information on the pixel corresponding to the method for reading the pixel in the conversion unit, the correction of the defective pixel can be performed. As a result, an imaging apparatus (imaging system), a method for processing thereof, and a readable memory device for storing a program can be provided, which reduces the defective pixel at the time of the pixel-addition reading and is more numerous in the pixel information in the image data, and moreover, scarcely deteriorates in resolution of the image data.

Next, in the fourth to sixth embodiments described below, a description will be made on a gain correction in case of performing the pixel-addition. The problem area of the gain correction in case of performing the pixel-addition as found by the inventor will be described below.

As described earlier, the gain correction is a processing for correcting fluctuation of the sensitivity of a photoelectric conversion element and gain fluctuation of a signal processing circuit unit. This gain correction usually irradiates radiation and performs radiographing in a state in which no subject exists before radiographing the subject, and performs a division processing for the image which has radiophotographed the subject by using the radiophotographed image as a gain correction image.

When the pixel-addition reading is performed in the radiation imaging apparatus of the present invention, for example, there is a problem in that the image after correction used actually by a doctor in his diagnosis is affected not only by the S/N of the subject image, but also by the S/N of the gain correction image. Further, there is a problem in that, when a component other than the gain correction image mixes with the gain correction image, this emerges in the image after correction as an artifact.

The fourth to sixth embodiments described below have been carried out in view of the above described problems, and these embodiments aim at providing a radiation imaging apparatus, which is high in S/N when performing the gain correction in the radiographing by the pixel-addition, and moreover, realizes acquisition of a radiographed image small in artifact.

Fourth Embodiment

Figure 18:
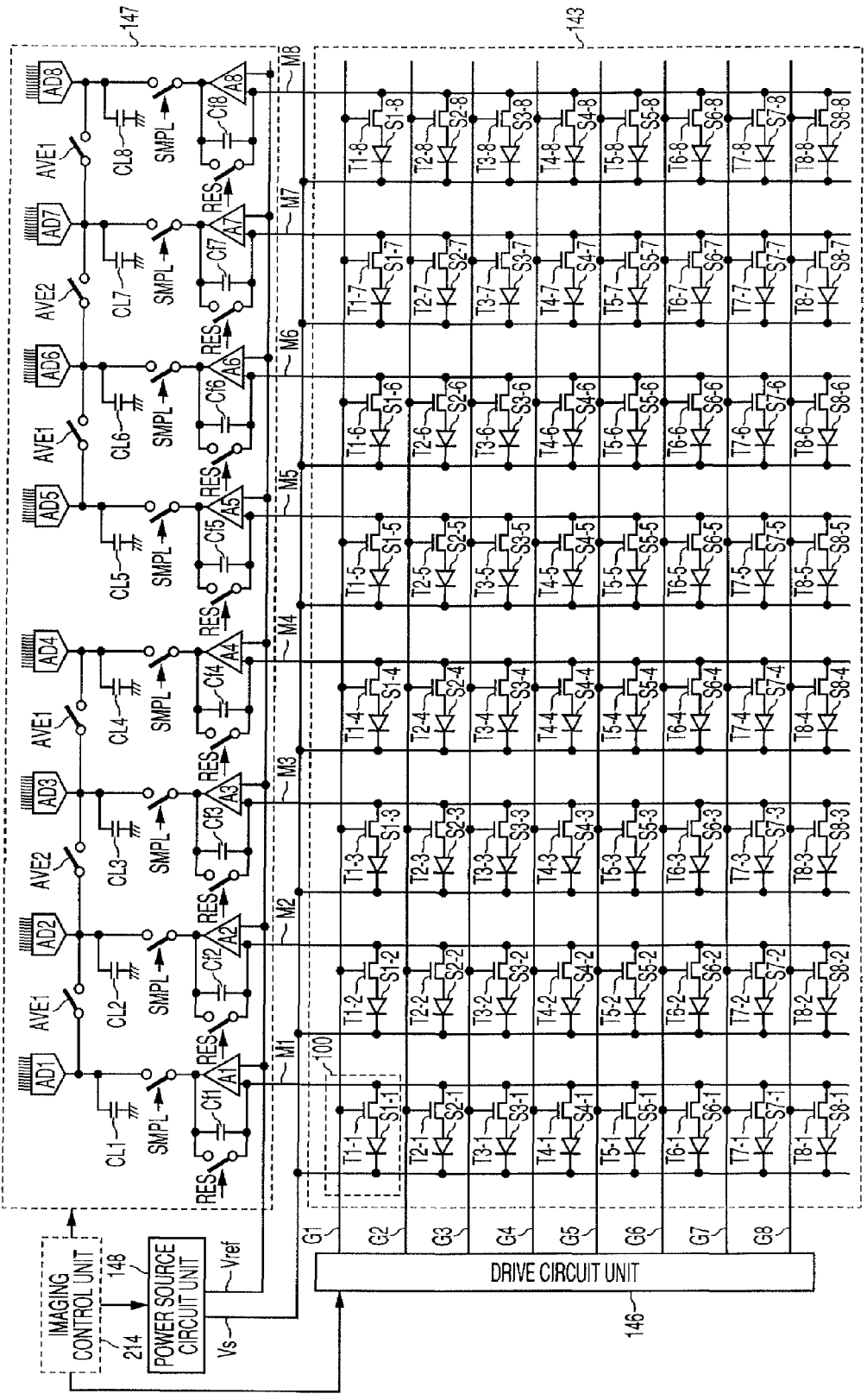
FIG. 18 is an equivalent value circuit diagram illustrating the detailed configuration in the radiation imaging apparatus of the radiation imaging system according to a fourth embodiment.

FIG. 18 is an equivalent circuit diagram illustrating a detailed configuration in a radiation imaging apparatus 140 of a radiation imaging system according to a fourth embodiment.

Here, in FIG. 18, from among each component comprising the radiation imaging apparatus 140, a photoelectric conversion circuit unit 143, a drive circuit unit 146 provided in an external circuit unit 145, signal processing circuit unit 147, and a power source circuit unit 148 are illustrated. The photoelectric conversion circuit unit 143, drive circuit unit 146, signal processing circuit unit 147, and the power source circuit unit 148 illustrated in FIG. 18, for example, are configured by using an amorphous silicon thin film semiconductor.

This radiation imaging apparatus 140, based on a control from an imaging control unit 214, is configured to be able to drive in various types of operation modes including a moving image radiographing mode and a still image radiographing mode.

The photoelectric conversion circuit unit 143 of FIG. 18 is disposed in a two-dimensional matrix pattern with photoelectric conversion elements S1-1 to S8-8 which are conversion elements for converting radiation into an electric signal (electric charge) and elements (unit-pixel) 100 provided with one piece each of switch elements T1-1 to T8-8 for taking out (transferring) the electric signal from the photoelectric conversion element. In FIG. 18, for convenience, a total of 64 unit-pixels of eight by eight pixels are illustrated.

Each unit-pixel 100 of this photoelectric conversion circuit unit 143, for example, is formed on an insulating substrate such as glass by using the amorphous silicon thin film semiconductor. Further, the photoelectric conversion elements S1-1 to S8-8 are formed by a MIS type structure or PIN type structure based on amorphous silicon as a main ingredient. In this case, on the photoelectric conversion elements S1-1 to S8-8, a wavelength converter 142 in which the photoelectric conversion element converts radiation into a light of the detectable wavelength region is provided, and the photoelectric conversion element is incident with a visible light from the wavelength converter 142. Incidentally, the photoelectric conversion elements S1-1 to S8-8 may be those absorbing the incident radiation (x-ray) and converting it directly into an electric charge. As the photoelectric conversion element of this direct conversion type, for example, one type selected from among amorphous selenium, gallium arsenide, mercuric iodide, lead iodide, and cadmium telluride is made as a main ingredient. Further, as the switch elements T1-1 to T8-8, a TFT (thin film transistor) formed on an insulating substrate such as glass by amorphous silicon is suitably used.

The photoelectric conversion elements S1-1 to S8-8, for example, comprise photodiodes, and are applied with a reverse bias. That is, the cathode electrode side of the photodiode is biased to + (plus). A bias wire Vs is a common wire for supplying a bias (Vs) to each photo diode, and is connected to a power source circuit unit 148.

Gate wires G1 to G8 are wires for connecting a switch element of each pixel in a row direction, and for turning on and off each of the switch elements T1-1 to T8-8. The drive circuit unit 146 applies a drive signal (pulse) to the gate wires G1 to G8 and drive-controls the switch elements T1-1 to T8-8. Signal wires M1 to M8 are wires for connecting the switch element of each pixel in a column direction and reading the electric signals (electric charges) of the photoelectric conversion elements S1-1 to S8-8 toward the signal processing circuit unit 147 through the switch elements T1-1 to T8-8.

A switch RES is for resetting capacitors Cf1 to Cf8. The amplifiers A1 to A8 is for amplifying electric signals from the signal wires M1 to M8. A Vref wire is a wire for supplying a reference power source from a power source circuit unit 104 to amplifiers A1 to A4. Capacitors CL1 to CL8 are sampling and holding capacitors for temporarily storing the electric signals amplified by the amplifiers A1 to A8. A switch SMPL is for performing a sampling and holding. Switches AVE1 and AVE2 are for pixel-addition (averaging out) the sampled and held electric signals. AD converters AD1 to AD8 are for converting the electric signals (analog signals) sampled and held by the sampling and holding capacitors CL1 to CL8 into digital signals. These digital signals after AD conversion are outputted, for example, to the image processing unit 10, and are subjected to the predetermined processing such as image processing, and after that, displaying and storing of the processed image data are performed.

Next, the operation of the radiation imaging system according to the present embodiment will be described. FIG. 19 is a view illustrating the operation mode of the radiation imaging system according to the fourth embodiment. As illustrated in FIG. 19, the radiation imaging system according to the present embodiment is configured to be able to set four operation modes of a still image radiographing mode, a first moving image radiographing mode (1), a second moving image radiographing mode (2), and a third moving image radiographing mode (3).

In the still image radiographing mode, since an image is radiographed only one sheet, there is no need to quicken a frame rate, and yet a resolving power is required, and therefore, no addition drive of the unit-pixel is performed. Further, the moving radiographing mode has a total of three types from the first and third, and each type is different in the addition number of unit-pixels.

In the addition processing of the unit-pixel, since signals of plurality of unit-pixels are simultaneously read, the frame rate becomes fast, and the S/N is also increased. However, since a plurality of unit-pixels are aggregated into one and outputted, a resolving power is reduced. Hence, depending on the conditions and the like of the subject (object) 126, a radiophotographer 305 who is an engineer selects which item from among the frame rate, S/N, and resolving power is given priority and radiophotographed by using the operator interface (I/F) 311. In the present embodiment, the addition number of unit-pixels becomes a pixel non-addition in the first moving radiographing mode (1), and two by two pixel-addition in the second moving radiographing mode (2), and four by four pixel-addition in the third moving image radiographing mode (3). That is, the operator interface (I/F) 311 has a function of operation mode setting means for setting the above described plurality of operation modes different in the addition number of pixel information on the unit-pixel 100 in the signal processing circuit unit 147.

Next, by using the timing chart illustrated in FIGS. 20 to 22, the operation of the radiation imaging system according to the present embodiment will be described.

Figure 20:
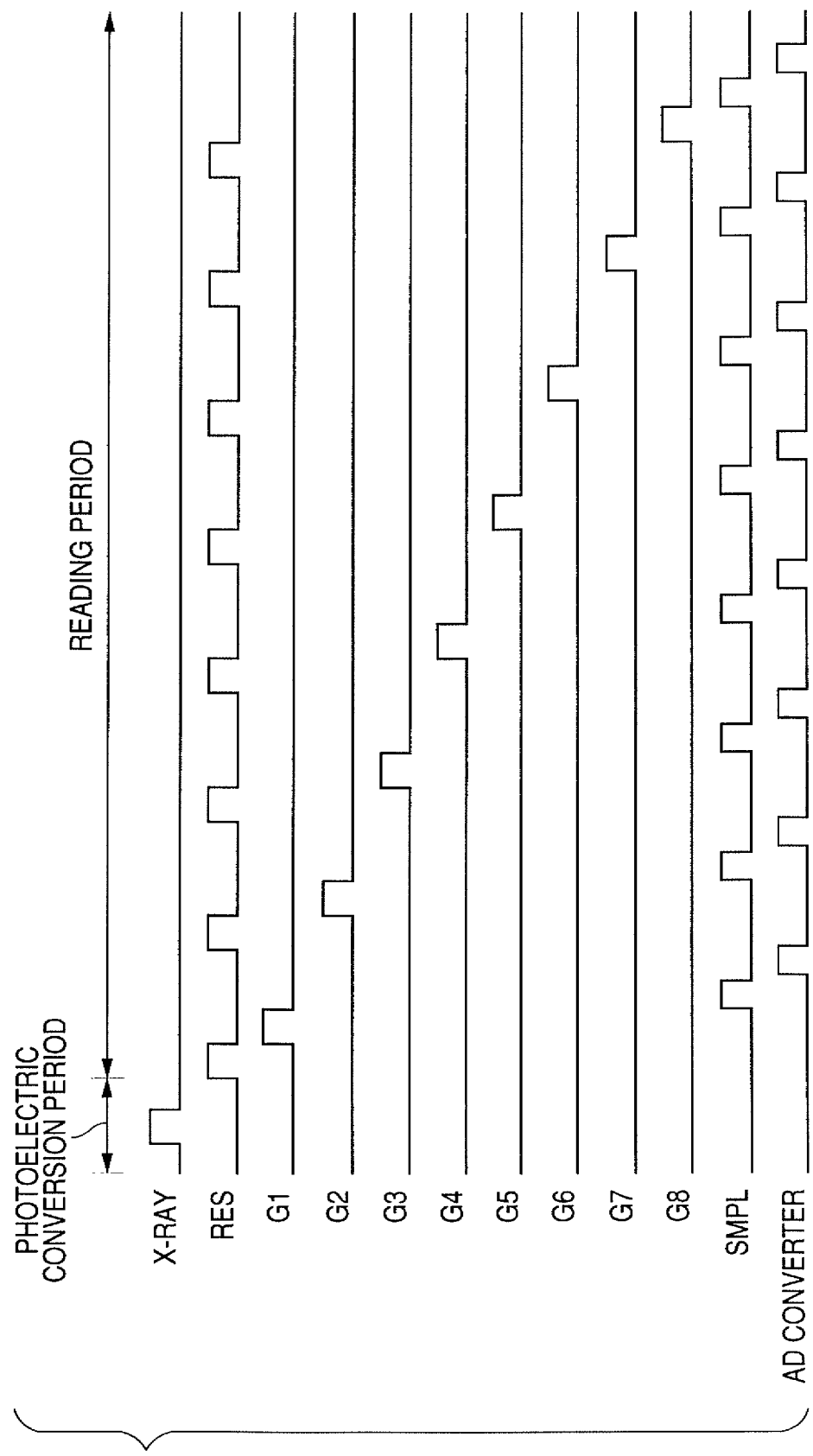
FIG. 20 is a timing chart illustrating a method for driving in a pixel non-addition of the radiation imaging system according to the fourth embodiment.

FIG. 20 is a timing chart illustrating a method for driving in the pixel non-addition of the radiation imaging system according to the fourth embodiment. Based on this timing chart, the operations of the photoelectric conversion circuit unit 143, the driving circuit unit 146 and the signal processing circuit unit 147 illustrated in FIG. 18 will be described.

First, the operation in a photoelectric conversion period (x-ray irradiation period) will be described. In a state in which all the switch elements are turned off, when radiation (x-ray) is irradiated pulse-wise from a radiation generating apparatus 120, each photoelectric conversion element is irradiated with radiation or a light converted in wavelength from radiation. Then, the electric signal (electric charge) corresponding to radiation or light quantity is accumulated in each photo electric conversion element.

At this time, when the above described wavelength converter 142 for converting the x-ray into a visible light is used, a member for guiding the visible light corresponding to the x-ray dose rate into the photoelectric conversion element side may be used or the wavelength converter 142 may be disposed extremely close to the photoelectric conversion element. Incidentally, even after the x-ray becomes non-irradiating, the electric signal (electric charge) subjected to photoelectric conversion is kept in each photoelectric conversion element.

Next, an operation during the reading period will be described. The reading operation is performed in order from the photoelectric conversion elements S1-1 to S1-8 of the first line, the photoelectric conversion elements S2-1 to S2-8 of the second line, and the photoelectric conversion elements S3-1 to S3-8 of the third line and it is performed until the reading operation of the photoelectric conversion elements S8-1 to S8-8 of the eighth line.

First, to read the electric signals (electric charges) accumulated in the photoelectric conversion elements S1-1 to S1-8 of the first line, a driving signal (pulse) is given to the gate wire G1 connected to the switch elements T1-1 to T1-8 of the first line from the drive circuit unit 146. At this time, the drive circuit unit 146, based on a control from the imaging control unit 214, outputs the drive signal to the gate wire G1. As a result, the switch elements T1-1 to T1-8 of the first line are put into a turned-on state, and the electric signals based on the electric charges accumulated in the photoelectric conversion elements S1-1 to S1-8 of the first line are transferred through the signal wires M1 to M8.

The electric signals transferred to these signal wires M1 to M8 are amplified by amplifiers A1 to A8 according to the capacitance of capacitors Cf1 to Cf8. The amplified electric signals are sample-held in the capacitors CL1 to C18 by a SMPL signal based on a control from the imaging control unit 214. After that, the electric signals sample-held by the capacitors CL1 to CL8 are AD-converted by the AD converters AD1 to AD8, and are outputted to the image processing unit 10 and the like as digital data.

Similarly to the reading operation of the photoelectric conversion elements S1-1 to S1-8 of the first line, the reading operation of the photoelectric conversion elements S2-1 to S2-8 of the second line, and the reading operation of the photoelectric conversion elements S3-1 to S3-8 of the third line are performed in order, and then, the reading operations of the fourth line to eighth line are performed.

In this manner, the x-ray is converted into the visible light by using the wavelength converter 142, and the visible light is converted into the electric charge by each photoelectric conversion element, and the x-ray information is read as the electric signal, so that the information on the object (subject 126) can be obtained.

Next, a method for driving in two by two pixels-addition will be described by using FIG. 21. FIG. 21 is a timing chart illustrating the method for driving in the two by two pixels-addition of the radiation imaging system according to the first embodiment.

The driving in the two by two pixels-addition, as compared with the case where the pixel-addition illustrated in FIG. 4 is not performed, is different in the number of gate wires which are simultaneously turned ON/OFF. As illustrated in FIG. 20, in the driving not performing the pixel-addition, though the gate wires are turned ON/OFF in order of G1, G2, G3, . . . , in the driving of the two by two pixel-addition, each group of G1 and G2, G3 and G4, G5 and G6, and G7 and G8 is simultaneously turned ON/OFF.

When the gate wires G1 and G2 are simultaneously turned ON by using the driving of such two by two pixels-addition, the switch elements T1-1 to T2-8 are simultaneously opened, and for example, a sum of the electric signals (electric signals two times the pixel non-addition) of the photoelectric conversion elements S1-1 and S2-1 is accumulated in the capacitor Cf1. Further, in the driving of the two by two pixel-addition, the reading period becomes also one half as compared to the case where the pixel-addition is not performed, and therefore, the frame rate becomes doubled.

Further, in the driving of the two by two pixels-addition, the pixel-addition is also performed in the direction of the signal wire. Specifically, after the electric signals are sample-held in the capacitors CL1 to CL8, the input of the AVE1 signal based on a control from the imaging control unit 214 allows the capacitances CL1 and CL2, CL3 and CL4, CL5 and CL6, and CL7 and CL8 to be coupled with one another, thereby to average out the sample-held signals. As a result, the electric signals for the two by two pixels are added up in one pixel, and outputted as the multi-pixel.

Next, the method for driving of the four by four pixels-addition will be described by using FIG. 22. FIG. 22 is a timing chart illustrating the method for driving in the four by four pixels-addition of the radiation imaging system according to the first embodiment.

In the driving in the two by two pixels-addition, while two pieces of the gate wires are simultaneously turned ON/OFF, in the driving in the four by four pixels-addition, the reading is performed by turning ON/OFF four pieces of the gate wires simultaneously. Hence, the signal output increased by four times is made. Further, as compared with the driving in the two by two pixels-addition, the reading period is shortened by ¼, and the frame rate is increased by four times.

With respect to the pixel-addition in the direction of the signal wire, after the electrical signals are sample-held in the capacitors CL1 to CL8, the input of the pulses of the AVE1 signal and AVE2 signal based on a control from the imaging control unit 214 allows each capacitance of the capacitors CL1 to CL4 and CL5 to CL8 to be coupled with one another. As a result, the electrical signals sample-held in each of the capacitors CL1 to CL-8 are averaged out, and the averaged analog signals are AD-converted, so that the electrical signals for the four by four pixels are added up into one pixel, and are outputted as the multi-pixel.

Figure 21:
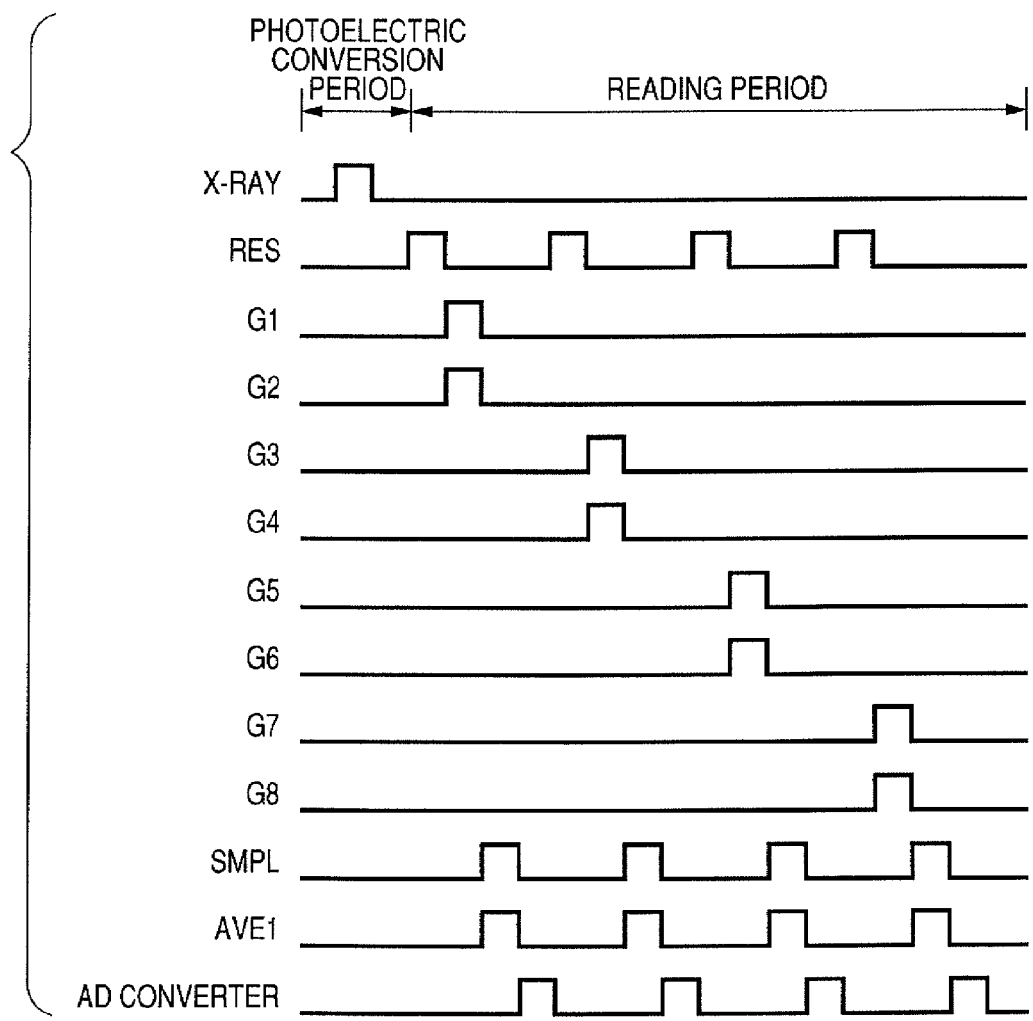
FIG. 21 is a timing chart illustrating the method for driving in a two by two-pixel-addition of the radiation imaging system according to the fourth embodiment.
Figure 22:
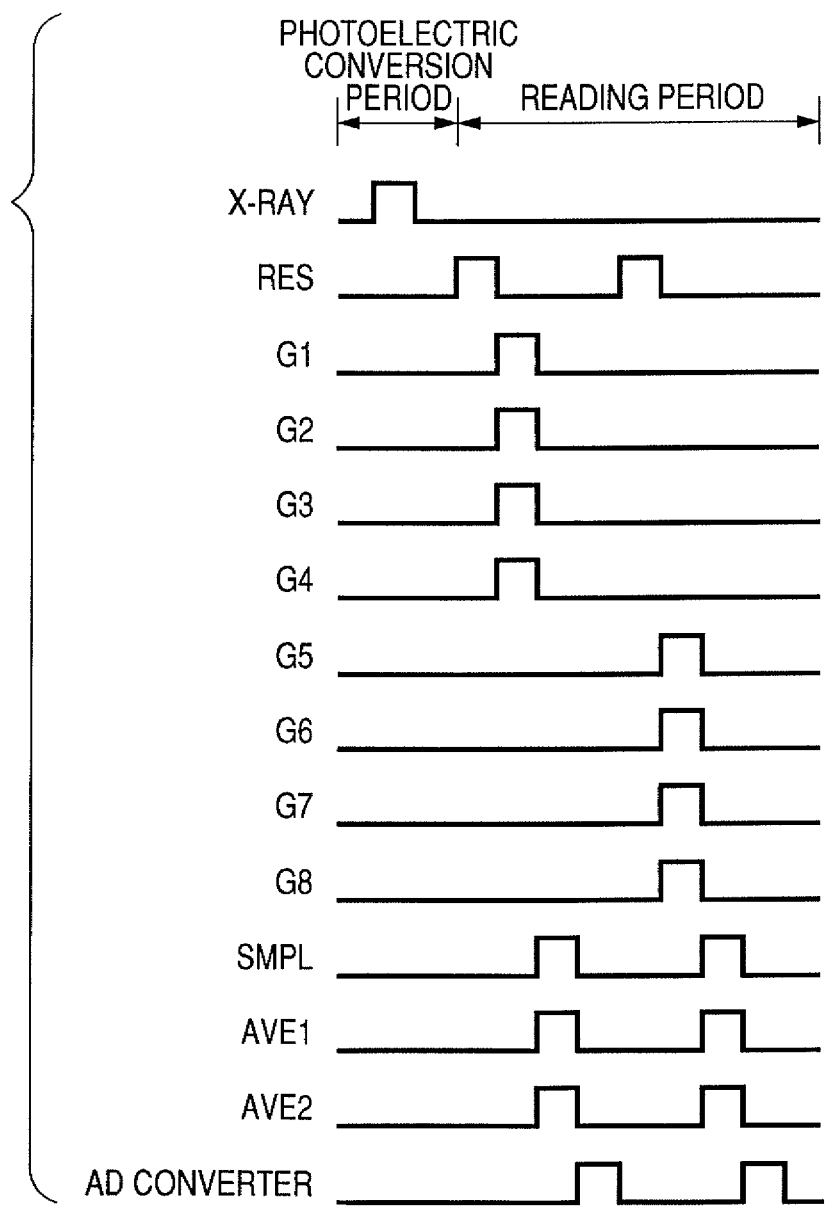
FIG. 22 is a timing chart illustrating the method for driving in a four by four-pixel-addition of the radiation imaging system according to the fourth embodiment.

Further, as evident from the driving timing of FIGS. 21 and 22, in the driving by the pixel-addition of the present embodiment, the addition processing is performed for the analog signals before the AD conversion by all AD converters AD1 to AD8. The reason why is because, as compared with the digital-addition for performing the pixel-addition after AD converting the analog signals of all unit-pixels, it is preferable to perform AD conversion after reducing the data amount by addition the analog signals since the AD conversion time and reading time are short and the frame rate can be made fast. Further, the addition processing of the analog signals can be made high in S/N as compared with the addition processing of the digital signals.

Figure 23A:
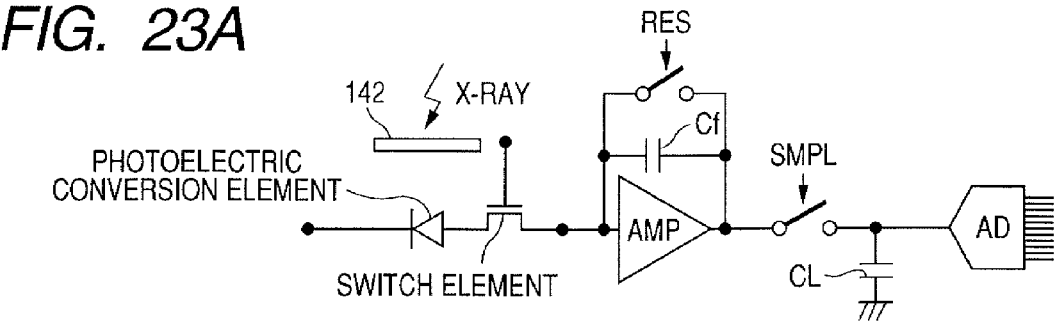
FIGS. 23A, 23B and 23C are schematic circuit diagrams illustrating the method for driving according to each pixel-addition mode.
Figure 23B:
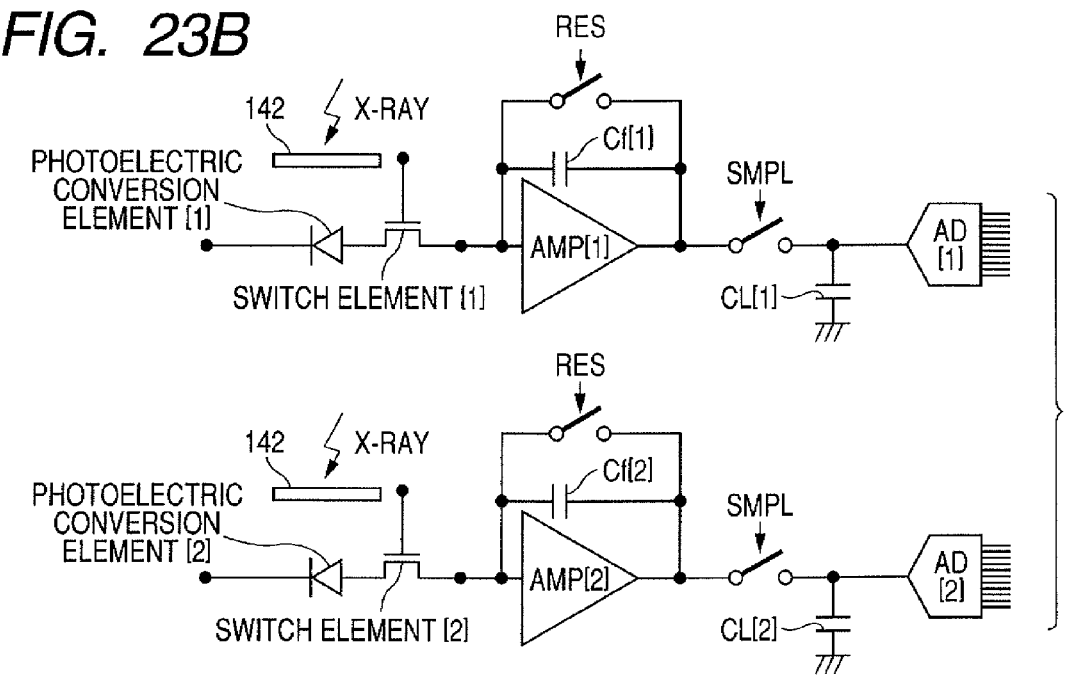
Figure 23C:
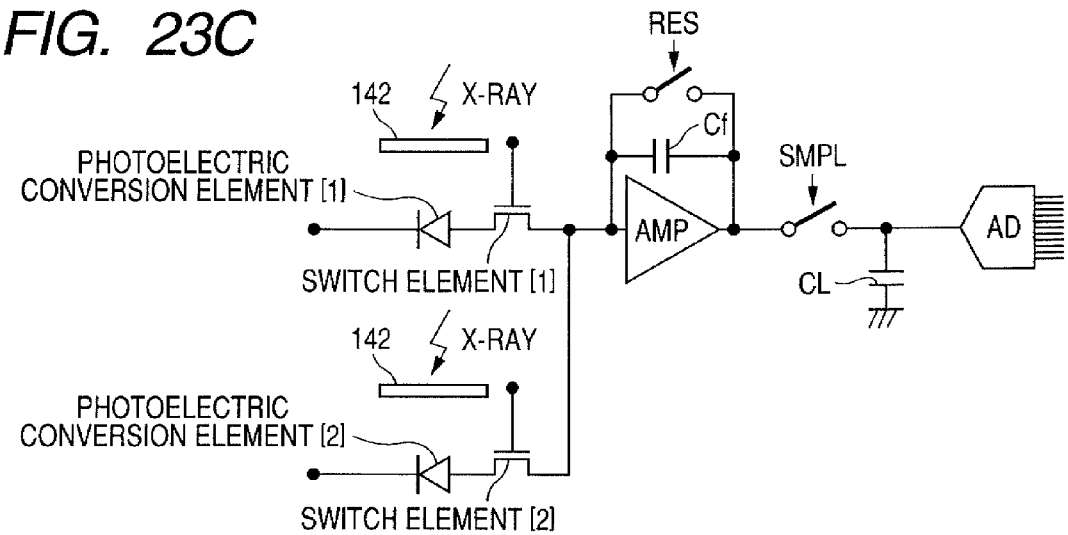

FIGS. 23A, 23B and 23C are schematic circuit diagrams illustrating the method for driving by each pixel-addition modes. Here, FIG. 23A is a schematic circuit diagram for a pixel non-addition mode, FIG. 23B for a digital-addition mode, and FIG. 23C for an analog-addition mode. A noise of the radiation imaging apparatus can be indicated in its outline by x-rays: a shot-noise at the x-ray irradiation time, senser: a shot-noise due to dark current of the photoelectric conversion element, and AMP (amplifier): a noise of the signal processing circuit, and AD: a quantized noise of the AD converter. The sum of the noise components is the square root of the sum of the squares of these components.

In the case of the circuit diagram of the pixel non-addition mode of FIG. 23A, each component is simply taken as a sum of squares so as to take the square root thereof. Further, in the case of FIG. 23B, at the subsequent stages of the AD converter AD (1) and AD (2), the digital-addition of two pixels are performed, and hence, all the noises are made ($\sqrt{2}$) times. FIG. 23C illustrates the analog-addition at the time of simultaneously turning on two pieces of the gate wires, and therefore, the x-ray: the shot-noise at the time of the x-ray irradiation and Senser: the noise associated with the x-ray and the photoelectric conversion element are made ($\sqrt{2}$) times. Specifically, the above described addition can be represented by the following formulas:

$$\text{Pixel non-addition} = \sqrt{\{(X\text{-RAY})\}^2 + (\text{Senser})^2 + (\text{AMP})^2 + (\text{AD})^2}$$

$$\text{Digital-addition} = \sqrt{\{2(X\text{-RAY})\}^2 + 2(\text{Senser})^2 + 2(\text{AMP})^2 + 2(\text{AD})^2}$$

$$\text{analog-addition} = \sqrt{\{2(X\text{-RAY})\}^2 + 2(\text{Senser})^2 + (\text{AMP})^2 + 2(\text{AD})^2}$$

Since a signal quantity according to each pixel-addition mode is such that the pixel non-addition=one time, the digital-addition=two times, and the analog-addition=two times, if compared with the S/N, the signal quantity is not less than the quantity where the pixel non-addition=1, the digital-addition=$2/(\sqrt{2})$, and the analog-addition=$2/(\sqrt{2})$. Hence, the S/N is the analog-addition>the digital-addition>the pixel non-addition. As a result, in view of the frame rate and the S/N, the driving by the pixel-addition is performed all by the analog addition.

Next, the radiographing of a gain correction image which is the feature of the present invention will be described.

In the present embodiment, as illustrated in FIG. 19, there are four types of operation modes, of which one type is a still image radiographing mode and the other three types are moving image radiographing modes. The feature of the present invention is to obtain a gain correction image by the same driving as each operation mode for radiographing an object in association with these four types of operation modes. Hence, by one still image radiographing mode and three moving image radiographing modes, the gain correction image is radiographed, and the gain correction image corresponding to each operation mode is obtained.

The actual diagnosis by a doctor is performed by the image after the gain correction is performed. Therefore, the S/N in the image after the gain correction processing becomes important. The S/N in the image after the gain correction is defined by the S/N of an object image radiographed by the engineer (operator 305) and the S/N of a gain correction image for the gain correction processing. Hence, when the S/N of the gain correction image is low, even when the S/N of the object image is high, an image quality is deteriorated.

Hence, in the present embodiment, in the case of the operation mode for performing the pixel-addition, the gain correction image performs not the radiographing by the digital-addition low in the S/N, but the radiographing by the analog-addition, which is similar to the radiographing of the object.

Further, when the gain correction image is made common with each operation mode and the object image actually radiographed by analog-addition is corrected by using the gain correction image of two by two pixel-addition which is produced by digital-addition from the radiographed image by pixel non-addition driving and the gain correction image of four by four pixel-addition, the artifact ends up developing. Here, a generation mechanism of the artifact will be described by using FIGS. 24A and 24B.

Figure 24A:
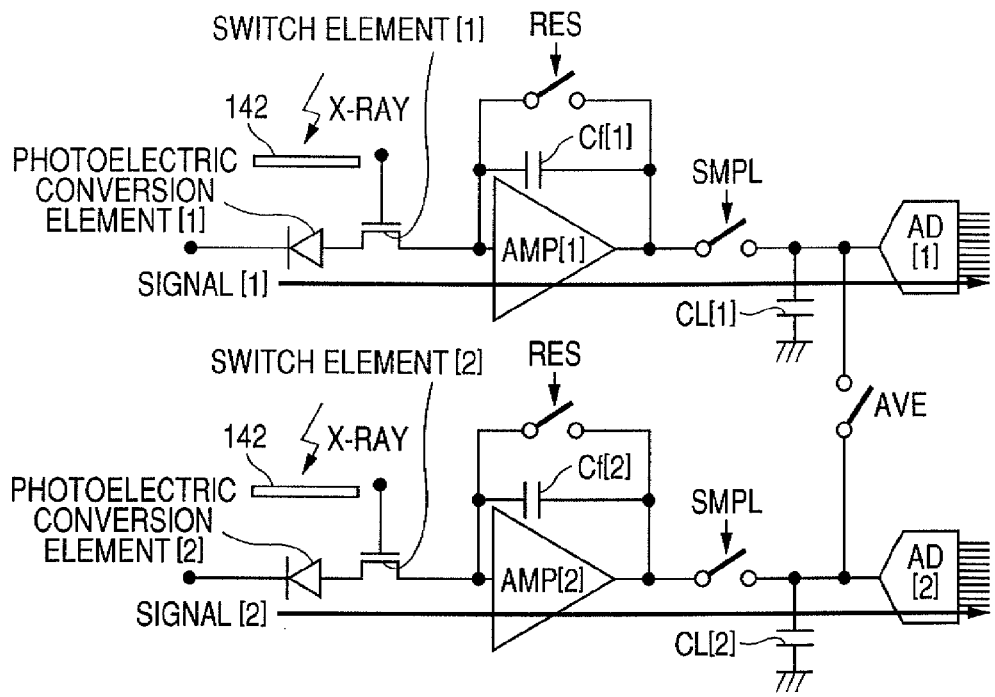
FIGS. 24A and 24B are schematic circuit diagrams for describing a generating mechanism of an artifact.
Figure 24B:
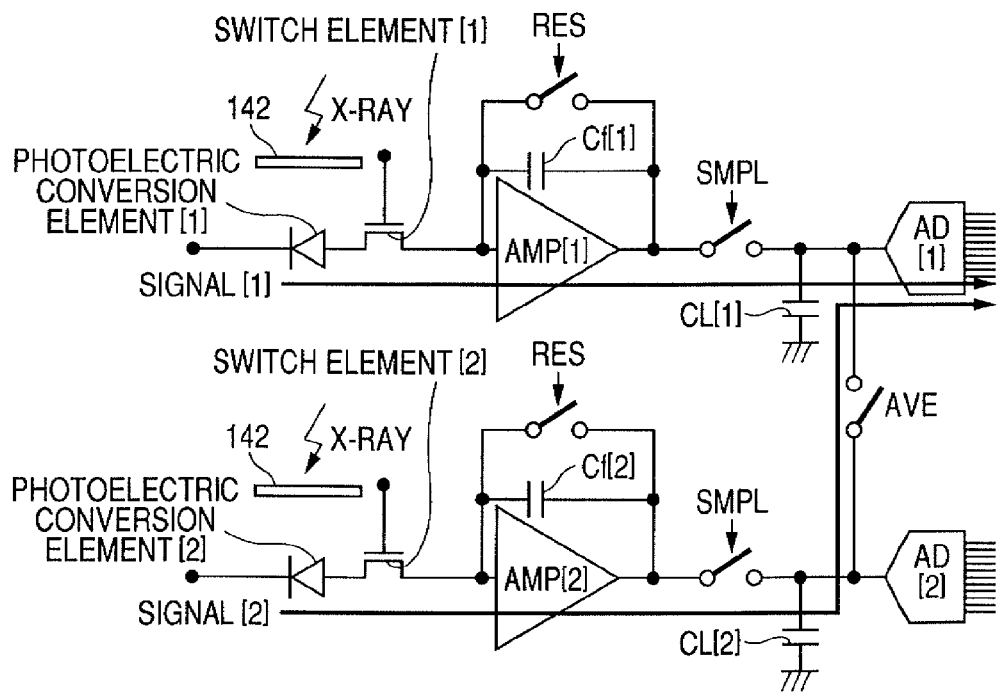

FIGS. 24A and 24B are schematic circuit diagrams for describing the generation mechanism of the artifact. In the case of the digital-addition illustrated in FIG. 24A, a signal (1) passes through a route of the photoelectric conversion element (1)→AMP (1)→AD (1), and a signal (2) passes through a route of the photoelectric conversion element (2)→AMP (2)→AD (2), and are outputted, respectively. In contrast to this, in the case of the analog-addition illustrated in FIG. 24B, the signal (1) passes through the route of the photoelectric conversion element (1)→AMP (1)→AD (1) and the same route as the digital-addition. However, the signal (2) becomes a photoelectric conversion element (2)→AMP (2)→AD (1), and is different in AD converter from the case of the digital-addition.

As representing a shift in the input and output of the actual AD converter as against the input and output of an ideal AD converter, there is an INL (Integral Non Linearity) characteristic. This characteristic changes in the characteristic by fluctuation of the element even if the same type of AD converter is used. Hence, if the characteristic is AD-converted and corrected by a different AD converter, the difference in those characteristics ends up developing in the image as an artifact (a striped artifact in this case). Due to fluctuation of the amplifiers and the elements of the capacitors also in addition to such fluctuation of the elements of the AD converter, when an attempt is made to subject an image by the digital-addition to the gain correction processing by an image by the analog-addition, an artifact ends up developing.

Hence, to improve the S/N and moreover eliminate the development of the artifact, in the present embodiment, in the case of the operation mode for performing the pixel-addition, when the object image is an image by the analog-addition, the gain correction image is also subjected to the correction processing by using the image by the analog-addition.

Next, an obtaining processing of the gain correction image will be described. FIG. 25 is a flowchart illustrating the obtaining processing of the gain correction image of the radiation imaging system according to the fourth embodiment. That is, FIG. 25 is a flowchart in calibration.

The obtaining of the gain correction image may be performed before the object is radiographed by the engineer (operator 305) or may be performed when the product is shipped from the plant. Further, since the sensitivity characteristic of the photoelectric conversion element is likely to change with time, a correct gain correction processing can be performed by making renewal every six months or annually.

Here, with respect to the radiographing itself of the calibration, except that the object (subject 126) is not placed between the radiation generating apparatus 120 and the radiation imaging apparatus 140, the radiation imaging apparatus is driven similarly to the case where the radiographing is performed by placing the ordinary object (subject 126). In the first embodiment, as described above, since the operation mode comprises four different modes, the radiation imaging apparatus is driven according to each mode, and the image is radiographed for one sheet each and is stored in the gain correction image memory (the external memory device 161 in the present embodiment). The processing of FIG. 25 will be specifically described below.

First, at step S101, a imaging control unit 214, based on a control from a system control unit 310, allows radiation to be generated from the radiation generating apparatus 120 in a state in which no subject 126 exists between the radiation generating apparatus 120 and the radiation imaging apparatus 140, and performs the radiographing by the still image radiographing mode. At step S102, an image processing unit 10, based on a control from the imaging control unit 214, stores the image radiographed by the still image radiographing mode of step S101 in the external memory device 161 as the gain correction image for the still image radiographing mode.

Subsequently, at step S103, the imaging control unit 214, based on a control from the system control 310, allows radiation to be generated from the radiation generating apparatus 120 in a state in which no subject 126 exists between the radiation generating apparatus 120 and the radiation imaging apparatus 140, and performs the radiographing by a first moving image radiographing mode (1). That is, the moving image radiographing by pixel non-addition is performed. At step S104, the image processing unit 10, based on a control from the imaging control unit 214, stores the image radiographed by the first moving image radiographing mode (1) of step S103 in the external memory device 161 as the gain correction image for the first moving image radiographing mode.

Subsequently, at step S105, the imaging control unit 214, based on a control from the system control unit 310, allows radiation to be generated from the radiation generating apparatus 120 in a state in which no subject 126 exists between the radiation generating apparatus 120 and the radiation imaging apparatus 140, and performs the radiographing by a second moving image radiographing mode (2). That is, the moving image radiographing by two by two pixel-addition is performed. At step S106, the image processing unit 10, based on a control from the imaging control unit 214, stores the image radiographed by the second moving image radiographing mode (2) of step S105 in the external memory device 161 as the gain correction image for the second moving image radiographing mode.

Subsequently, at step 107, the imaging control unit 214, based on a control from the system control unit 310, allows radiation to be generated from the radiation generating apparatus 120 in a state in which no subject 126 exists between the radiation generating apparatus 120 and the radiation imaging apparatus 140, and performs the radiographing by a third moving image radiographing mode (3). That is, the moving image radiographing by four by four pixel-addition is performed. At step S108, the image processing unit 10, based on a control from the imaging control unit 214, stores the image radiographed by the third moving image radiographing mode (3) of step S107 in the external memory device 161 as the gain correction image for the third moving image radiographing mode.

By going through the processings of the above described steps S101 to S108, the image data according to the gain correction image corresponding to each operation mode is stored in the external memory device 161.

Next, an actual radiographing operation in case the object (subject 126) is disposed will be described. FIG. 26 is a flowchart illustrating the processing in the radiographing operation of the radiation imaging system according to the fourth embodiment.

First, before starting the radiographing, the system control unit 310 accepts radiographing conditions such as object information, x-ray tube voltage, x-ray tube current, irradiation time, and image processing conditions of the radiation generating apparatus 120 inputted through an operator interface (I/F) 311 by the engineer (operator 305) (S201). Further, the system control unit 310 detects the operation mode selected from among four operation modes by the engineer (operator 305) through the operator interface (I/F) 311 (S202).

Subsequently, at step S203, for example, the imaging control unit 214 determines whether or not the operation mode detected and selected at step S202 is the still image radiographing mode.

At step S203, when it is determined that the selected operation mode is the still image radiographing mode, subsequently at step S204, the imaging control unit 214 controls the radiation generating apparatus 120 and radiation imaging apparatus 140, and performs x-rays radiographing by the still image radiographing mode. Specifically, the imaging control unit 214 irradiates x-rays from x-rays tube 121 of the radiation generating apparatus 120, and performs a control for reading the electric signal of the unit-pixel of the photoelectric conversion circuit unit 143 by pixel non-addition, and obtains the radiographed image by the still image radiographing mode.

Subsequently, at step S205, the image processing unit 10, based on a control from the imaging control unit 214, performs an offset correction processing for the image data of the radiographed image radiographed at step S204. Specifically, the image processing unit 10 performs an offset correction a dark component of the photoelectric conversion element and an offset component such as the amplifier of the signal processing circuit unit 147 for the image data of the radiographed image radiographed at step S204.

Subsequently, at step S206, the image processing unit 10, based on a control from the imaging control unit 214, performs a gain correction for the image data subjected to the offset correction processing at step S205. Specifically, the image processing unit 10 first extracts the image data of the gain correction image for the still image radiographing mode from among the external memory device 161. Next, the image processing unit 10 subjects the image data by the still image radiographing mode subjected to the offset correction processing at step S205 based on the gain correction image for the extracted still image radiographing mode.

Subsequently, at step S207, the image processing unit 10, based on a control from the imaging control unit 214, performs other image processings adapted to the image processing conditions for the image data subjected to the gain correction processing at step S206. Subsequently, at step S208, the system control unit 310 or the imaging control unit 214 controls the image processing unit 10, and displays the radiographed image by the still image radiographing mode subjected to the predetermined image processing in a display unit 160 or a monitor 174. In the case of the still image radiographing mode, when the radiographed image is radiographed one sheet, the radiographing operation is completed.

On the other hand, at step S203, when it is determined that the selected operation mode is not the still image radiographing mode, the control unit advances to step S209. At step S209, for example, the imaging control unit 214 determines whether or not the operation mode detected and selected at step S202 is the first moving image radiographing mode (1).

When it is determined that the operation mode selected at step S209 is the first moving image radiographing mode (1), the control unit advances to step S210. At step S210, the imaging control unit 214 controls the radiation generating apparatus 120 and the radiation imaging apparatus 140, and performs the x-ray radiographing by the first moving image radiographing mode (1). Specifically, the imaging control unit 214 irradiates the x-ray from the x-ray tube 121 of the radiation generating apparatus 120, and performs a control for reading the electric signals of the unit-pixels of the photoelectric conversion circuit unit 143 by pixel-non addition, and obtains the radiographed image by the first moving image radiographing mode (1).

Subsequently, at step S211, the image processing unit 10, based on a control from the imaging control unit 214, performs the offset correction processing for the image data of the radiographed image radiographed at step S210. Specifically, the image processing unit 10 performs the offset correction subtracting a dark component of the photoelectric conversion element and an offset component such as the amplifier of the signal processing circuit unit 147 for the image data of the radiographed image radiographed at step S210.

Subsequently, at step S212, the image processing unit 10, based on a control from the imaging control unit 214, performs the gain correction processing for the image data subjected to the offset correction processing at step S211. Specifically, the image processing unit 10 first extracts the image data of the gain correction image for the first moving image radiographing mode from within the external memory device 161. Then, the image processing unit 10 subjects the image data by the first moving radiographing mode subjected to the offset correction processing at step S211 to the gain correction processing based on the gain correction image for the first extracted moving image radiographing mode.

Subsequently, at step S213, the image processing unit 10, based on a control from the imaging control unit 214, performs other image processings adapted to the image processing conditions for the image data subjected to the gain correction processing at step S212. Subsequently, at step S214, the system control unit 310 or the imaging control unit 214 controls the image processing unit 10, and displays the radiographed image by the first moving image radiographing mode (1) subjected to the predetermined image processing at a display unit 160 or monitor 174.

Subsequently, at step S215, for example, the system control unit 310 determines whether or not the instruction (for separating an irradiation switch) for termination of the radiographing by the first moving image radiographing mode (1) is issued by the engineer (operator 305) through the operator interface (I/F) 311. As a result of this determination, when no instruction for termination of the radiographing by the first moving image radiographing mode (1) is issued, the control unit 310 returns to step S210, and renews in real time the display of the monitor 174 or the like, while repeating the radiographing→imaging processing→display. On the other hand, as a result of the determination of step S215, when the instruction for the termination of the radiographing by the first moving image radiographing mode (1) is issued, the radiographing operation is terminated.

On the other hand, at step S209, when it is determined that the selected operation mode is not the first moving image radiographing mode (1), the control unit advances to step S216. At step S216, for example, the imaging control unit 214 determines whether or not the operation mode detected and selected at step S202 is the second moving image radiographing mode (2).

When it is determined that the operation mode selected at step S216 is the second moving image radiographing mode (2), the control unit advances to step S217. At step S217, the imaging control unit 214 controls the radiation generating apparatus 120 and the radiation imaging apparatus 140, and performs the x-ray radiographing by the second moving image radiographing mode (2). Specifically, the imaging control unit 214 irradiates the x-ray from the x-ray tube 121 of the radiation generating apparatus 120, and performs a control for reading the electric signal of the unit-pixel of the photoelectric conversion circuit unit 143 by two by two pixel-addition, and obtains the radiographed image by the second moving image radiographing mode (2).

Subsequently, at step S218, the image processing unit 10, based on a control from the imaging control unit 214, performs the offset correction processing for the image date of the radiographed image radiographed at step S217. Specifically, the image processing unit 10 performs the offset correction subtracting a dark component of the photoelectric conversion element and an offset component such as the amplifier of the signal processing circuit unit 147 for the image data of the radiographed image radiographed at step S217.

Subsequently, at step S219, the image processing unit 10, based on a control from the imaging control unit 214, performs the gain correction processing for the image data subjected to the offset correction processing at step S218. Specifically, the image processing unit 10 first extracts the image data of the gain correction image for the second moving image radiographing mode from within the external memory device 161. Then, the image processing unit 10 subjects the image data by the second moving image radiographing mode subjected to the offset correction processing at step S218 to the gain correction processing based on the gain correction image for the second extracted moving image radiographing mode.

Subsequently, at step S220, the image processing unit 10, based on a control from the imaging control unit 214, performs other image processings adapted to the image processing conditions for the image data subjected to the gain correction processing at step S219. Subsequently, at step S221, the system control unit 310 or the imaging control unit 214 controls the image processing unit 10, and displays the radiographed image by the second moving image radiographing mode (2) subjected to the predetermined image processing at a display unit 160 or monitor 174.

Subsequently, at step S222, for example, the system control unit 310 determines whether or not the instruction (for separating an irradiation switch) for termination of the radiographing by the second moving image radiographing mode (2) is issued by the engineer (operator 305) through the operator interface (I/F) 311. As a result of this determination, when no instruction for termination of the radiographing by the second moving image radiographing mode (2) is issued, the control unit 310 returns to step S217, and renews in real time the display of the monitor 174 or the like, while repeating the radiographing→imaging processing→display. On the other hand, as a result of the determination of step S222, when the instruction for the termination of the radiographing by the second moving image radiographing mode (2) is issued, the radiographing operation is terminated.

When it is determined that the operation mode selected at step S216 is not the second moving image radiographing mode (2), since the operation mode selected at step S202 is the remaining third moving image radiographing mode (3), the control unit advances to step S223. At step S223, the imaging control unit 214 controls the radiation generating apparatus 120 and the radiation imaging apparatus 140, and performs the x-ray radiographing by the third moving image radiographing mode (3). Specifically, the imaging control unit 214 irradiates the x-ray from the x-ray tube 121 of the radiation generating apparatus 120, and performs a control for reading the electric signal of the unit-pixel of the photoelectric conversion circuit unit 143 by four by four pixel-addition, and obtains the radiographed image by the third moving image radiographing mode (3).

Subsequently, at step S224, the image processing unit 10, based on a control from the imaging control unit 214, performs the offset correction processing for the image date of the radiographed image radiographed at step S223. Specifically, the image processing unit 10 performs the offset correction subtracting a dark component of the photoelectric conversion element and an offset component such as the amplifier of the signal processing circuit unit 147 for the image data of the radiographed image radiographed at step S223.

Subsequently, at step S225, the image processing unit 10, based on a control from the imaging control unit 214, performs the gain correction processing for the image data subjected to the offset correction processing at step S224. Specifically, the image processing unit 10 first extracts the image data of the gain correction image for the third moving image radiographing mode from within the external memory device 161. Then, the image processing unit 10 subjects the image data by the third moving image radiographing mode subjected to the offset correction processing at step S224 to the gain correction processing based on the gain correction image for the extracted third moving image radiographing mode.

Subsequently, at step S226, the image processing unit 10, based on a control from the imaging control unit 214, performs other image processings adapted to the image processing conditions for the image data subjected to the gain correction processing at step S225. Subsequently, at step S227, the system control unit 310 or the imaging control unit 214 controls the image processing unit 10, and displays the radiographed image by the third moving image radiographing mode (3) subjected to the predetermined image processing at the display unit 160 or monitor 174.

Subsequently, at step S228, for example, the system control unit 310 determines whether or not the instruction (for separating an irradiation switch) for termination of the radiographing by the third moving image radiographing mode (3) is issued by the engineer (operator 305) through the operator interface (I/F) 311. As a result of this determination, when no instruction for termination of the radiographing by the third moving image radiographing mode (3) is issued, the control unit 310 returns to step S223, and renews in real time the display of the monitor 174 or the like, while repeating the radiographing→imaging processing→display. On the other hand, as a result of the determination of step S228, when the instruction for the termination of the radiographing by the third moving image radiographing mode (3) is issued, the radiographing operation is terminated.

Fifth Embodiment

Next, a fifth embodiment of the present invention will be described.

The configuration of a radiation imaging system according to the fifth embodiment is the same as the radiation imaging system according to the fourth embodiment. Further, the processing in the radiographing operation of the radiation imaging system according to the fifth embodiment is the same as the processing in the radiographing operation of the radiation imaging system according to the fourth embodiment. In the radiation imaging system according to the fifth embodiment, that which is different from the radiation imaging system according to the fourth embodiment is an obtaining processing of the gain correction image, and therefore, the description thereof only will be made as follows.

FIG. 27 is a flowchart illustrating the obtaining processing of the gain correction image of the radiation imaging system according to the fifth embodiment. That is, FIG. 27 is a flowchart in calibration.

First, at step S301, a imaging control unit 214, based on a control from a system control unit 310, allows radiation to be generated from a radiation generating apparatus 120 in a state in which no subject 126 exists between the radiation generating apparatus 120 and a radiation imaging apparatus 140, and performs radiographing by a still image radiographing mode for ten sheets. Subsequently, at step S302, for example, an image processing unit 10, based on a control from the imaging control unit 214, subjects the ten images radiographed at step S301 to an averaging processing. At step S303, the image processing unit 10, based on a control from the imaging control unit 214, stores the image subjected to the averaging processing at step S302 in an external memory device 161 as a gain correction image for the still image radiographing mode.

Subsequently, at step S304, the imaging control unit 214, based on a control from a system control unit 310, allows radiation to be generated from the radiation generating apparatus 120 in a state in which no subject 126 exists between the radiation generating apparatus 120 and the radiation imaging apparatus 140, and performs the radiographing by the first moving image radiographing mode (1) for ten sheets. That is, the moving image radiographing by the pixel non-addition is performed for ten sheets. Subsequently, at step S305, for example, the image processing unit 10, based on a control from the imaging control unit 214, subjects the ten sheets of the images radiographed at step S304 to the averaging processing. At step S306, the image processing unit 10, based on a control from the imaging control unit 214, stores the image subjected to the averaging processing at step S305 in the external memory device 161 as the gain correction image for the first moving image radiographing mode.

Subsequently, at step S307, the imaging control unit 214, based on a control from a system control unit 310, allows radiation to be generated from the radiation generating apparatus 120 in a state in which no subject 126 exists between the radiation generating apparatus 120 and the radiation imaging apparatus 140, and performs the radiographing by a second moving image radiographing mode (2) for ten sheets. That is, the moving image radiographing by two by two pixel-addition is performed for ten sheets. Subsequently, at step S308, for example, the image processing unit 10, based on a control from the imaging control unit 214, subjects the ten sheets of the image radiographed at step S307 to the averaging processing. At step S309, the image processing unit 10, based on a control from the imaging control unit 214, stores the image subjected to the averaging processing at step S308 in the external memory device 161 as the gain correction image for the second moving image radiographing mode.

Subsequently, at step S310, the imaging control unit 214, based on a control from a system control unit 310, allows radiation to be generated from the radiation generating apparatus 120 in a state in which no subject 126 exists between the radiation generating apparatus 120 and the radiation imaging apparatus 140, and performs the radiographing by the third moving image radiographing mode (3) for ten sheets. That is, the moving image radiographing by four by four pixel-addition is performed for ten sheets. Subsequently, at step S311, for example, the image processing unit 10, based on a control from the imaging control unit 214, subjects the ten sheets of the image radiographed at step S310 to the averaging processing. At step S312, the image processing unit 10, based on a control from the imaging control unit 214, stores the image subjected to the averaging processing at step S311 in the external memory device 161 as the gain correction image for the third moving image radiographing mode.

By going through the processings of steps S301 to S312, the image data according to the gain correction image corresponding to each operation mode is stored in the external memory device 161.

In the fourth embodiment, when the gain correction image is radiographed, one sheet of the image is radiographed for each operation mode. On the other hand, in the fifth embodiment, as illustrated in the flowchart of FIG. 27, ten sheets each of the same gain correction image are radiographed for each operation mode, and that image is subjected to the averaging processing and is stored in the external memory device 161 (gain correction image memory) as the gain correction image.

A plurality of sheets (N sheets) are radiographed and subjected to the averaging processing, so that the noise component ($\sigma$) of the image is reduced to $1/(\sqrt{2})$. For example, as illustrated in the present embodiment, when ten sheets of the image are subjected to the averaging processing, the noise component is reduced to $1/(\sqrt{10})$ or when 100 sets of the image are subjected to the averaging processing, the noise component is reduced to $1/(\sqrt{100})=1/10$, and the effect of the noise of the gain correction image for the image after the gain correction is reduced. Further, in the case of the moving image radiographing mode, since the radiographing is continuously performed, the radiographing of one sheet as well as ten sheets can be performed with scarcely changing the time required for radiographing. For example, if the moving image driving performs the moving image radiographing by 30 FPS, the radiographing time for one sheet is 33 ms, and the radiographing time for 10 sheets is 330 ms, and therefore, the time increased is only 330 ms−33 ms=297 ms, and the number of man-hours required for a person in charge of performing the calibration scarcely changes.

Sixth Embodiment

Next, a sixth embodiment of the present invention will be described. The configuration of a radiation imaging system according to the sixth embodiment is the same as the radiation imaging system according to the fourth embodiment. Further, the obtaining processing of a gain correction image of the radiation imaging system and the processing in the radiographing operation according to the sixth embodiment are the same as the processing in the radiation imaging system according to the fourth embodiment. In the radiation imaging system according to the sixth embodiment, that which is different from the radiation imaging system according to the fourth embodiment is an inner configuration of a signal processing circuit unit 147, and therefore, the description thereof only will be described below.

Figure 28:
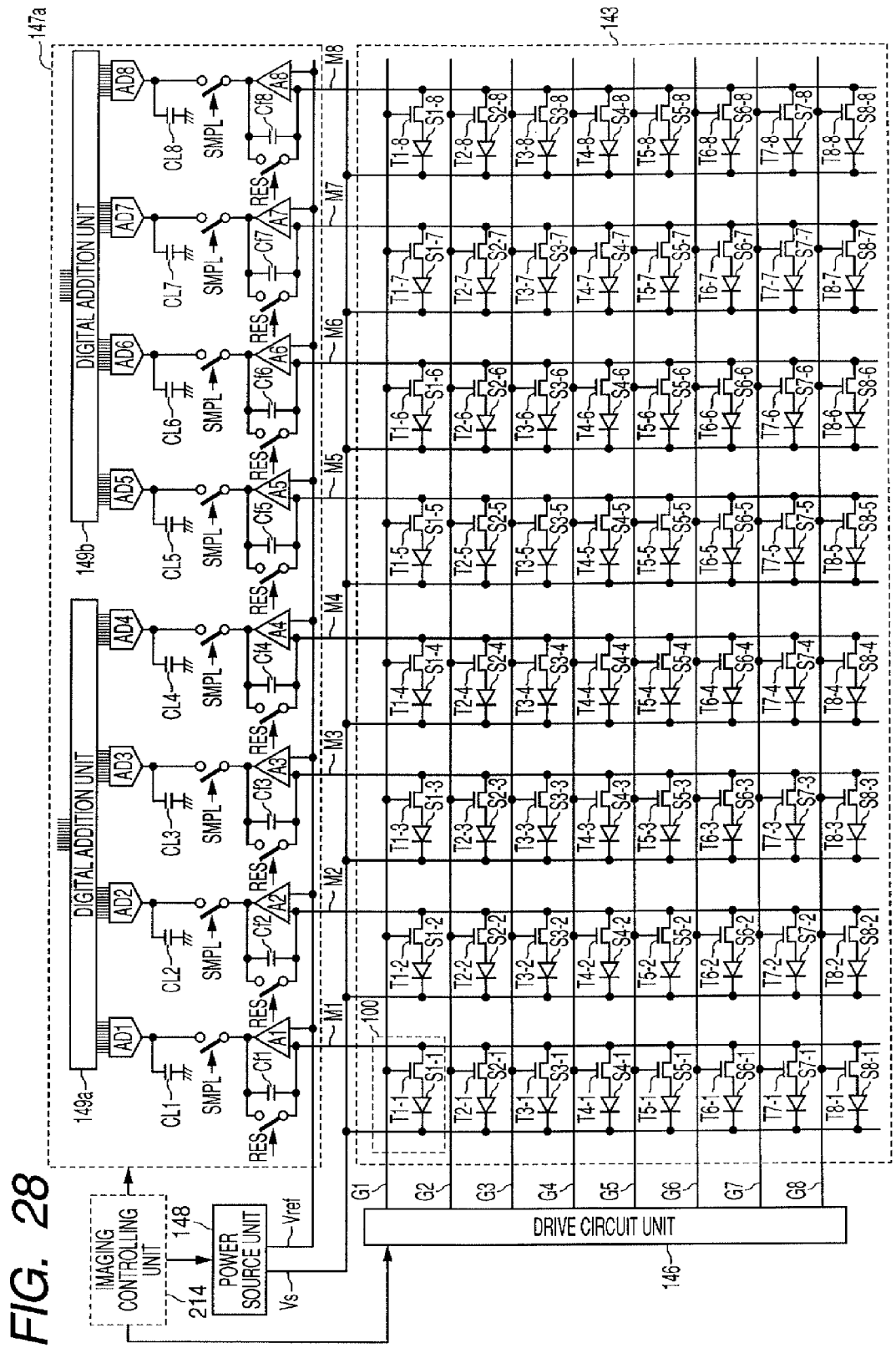
FIG. 28 is an equivalent value circuit diagram illustrating the detailed configuration in a radiation imaging apparatus 140 of the radiation imaging system according to a sixth embodiment.

FIG. 28 is an equivalent circuit diagram illustrating the detailed configuration in a radiation imaging apparatus 140 of the radiation imaging system according to the sixth embodiment. The feature of the radiation imaging apparatus 140 according to the sixth embodiment is that a signal processing circuit unit 147a comprises digital-addition circuit units 149a and 149b. That is, when compared with the equivalent circuit diagram of the fourth embodiment, there exist no switches AVE1 and AVE2 having performed the pixel-addition in the direction of the signal wire and the subsequent stages of AD converters AD1 to AD8 are provided with digital-addition circuit units 149a and 149b.

In the fourth embodiment, though the pixel addition has been performed by the switches AVE1 and AVE2 before performing AD conversion by the AD converters AD1 to AD8, in the sixth embodiment, the digital-addition is performed after performing the AD conversion by the AD converts AD1 to AD8. When the signal processing circuit unit 147 not provided with an averaging function such as the switches AVE1 and AVE2 is used before the AD conversion, the pixel-addition in the direction of the wire is performed by the digital-addition, and only in the direction of a gate wire, the analog-addition can be performed. These digital-addition circuit units 149a and 149b can perform the digital-addition also by a programmable device such as a PLD, and a degree of freedom of the design can be also broadened. Hence, the radiographing of an object radiographed image and a gain correction image in the sixth embodiment is performed by the digital-addition in the case of the pixel-addition in the direction of the signal wire, and by the analog-addition in the case of the pixel-addition in the direction of the gate wire, so that the development of an artifact in the image after the gain correction can be reduced.

According to the fourth to sixth embodiments of the present invention, when the gain correction is performed in the radiographing by the pixel-addition, the S/N is high, and moreover, the radiographed image few in artifact can be obtained.

Further, the above described fourth to sixth embodiments may be combined with any of the above described first to third embodiments.

Further, each means comprising the above described radiation imaging system according to the present invention and each step illustrating the method for processing of the radiation imaging system can be realized by activation of the program stored in RAM and ROM of a computer. This program and a storage medium recorded with the program readable by the computer are included in the present invention.

Specifically, the program is recorded in the storage medium such as, for example, CD-ROM or the program is provided to the computer through various transfer mediums. As the storage medium recording this program, a flexible disk, hard disk, magnetic tape, magnetic optical disk, non-volatile memory card and the like can be used in addition to CD-ROM. On the other hand, as the transfer medium of this program, a communication medium in a computer network (such as LAN, WAN such as internet, radio-communication network) system for propagating and providing program information as a carrier wave can be used. Further, as the communication medium at this time, a wire circuit and a wireless circuit such as an optical fiber can be cited.

Further, not only the case where the functions of the radiation imaging system according to the present invention can be realized by realizing the program provided to the computer, but also the case that the functions of the radiation imaging system according to the present invention are realized in corroboration with the OS (operating system) in which the program is working in the computer or other application soft, and as well as the case where a whole or a part of the processing of the provided program is performed by the feature expansion board and feature expansion unit of the computer so as to realize the functions of the radiation imaging system of the present invention, that is, all the cases as described above include such program in the present invention.

INDUSTRIAL APPLICABILITY

The present invention is used for a photoelectric conversion apparatus, radiation imaging apparatus, radiation imaging system, and program operating these apparatuses, which are used for a medical diagnostic apparatus, non-destructive analytical instrument, and the like.

The invention claimed is:

1. An imaging apparatus comprising:
a conversion unit comprising a plurality of unit-pixels for converting, into a signal, incident radiation or light according to the incident radiation or light;
a control unit for controlling said conversion unit according to a plurality of operation modes;
a signal processing unit, operating based on the control by said control unit, for reading a signal of unit-pixel from said conversion unit according to a unit-pixel reading mode among the plurality of operation modes, and for reading a signal of multi-pixel derived by adding signals of two or more unit-pixels from said conversion unit according to a pixel-addition reading mode among the plurality of operation modes;
a storage unit for storing positional information of a defective unit-pixel detected based on comparing, with a first threshold value, a signal of a unit-pixel read by the signal processing unit from said conversion unit irradiated with radiation or light, and for storing positional information of a defective multi-pixel detected based on comparing, with a second threshold value, a signal of a multi-pixel derived by adding signals of two or more unit-pixels read by said signal processing unit from said conversion unit irradiated with radiation or light; and
a pixel processing unit for performing a correction of a signal of unit-pixel read by said signal processing unit from the conversion unit, based on the positional information of the defective unit-pixel in the unit-pixel reading mode, and for performing a correction of a signal of multi-pixel derived by adding signals of two or more unit-pixels read by said signal processing unit from said conversion unit, based on the positional information of the defective multi-pixel in the pixel-addition reading mode.

2. The imaging apparatus according to claim 1, wherein
the first threshold value is a percentage ratio to an average signal averaged signals of normal unit-pixels, and
the second threshold value is a percentage ratio to average signal averaged signals derived by adding signals of two or more normal unit-pixels.

3. The imaging apparatus according to claim 2, wherein the first and second threshold values are in the same percentage ratio.

4. The imaging apparatus according to claim 1, wherein the signal of a multi-pixel derived by adding signals of two or more unit-pixels read by said signal processing unit from said conversion unit irradiated with radiation or light is calculated based on the signal of the unit-pixel read by said signal processing unit from the conversion unit irradiated with radiation or light.

5. The imaging apparatus according to claim 1, wherein the signal of a multi-pixel derived by adding two or more unit-pixels read by said signal processing unit from said conversion unit irradiated with radiation or light is an analog signal.

6. The imaging apparatus according to claim 1, wherein said conversion unit comprises:
a wave length converter for converting incident radiation into light; and
a photoelectric conversion element formed from amorphous silicon as a main ingredient.

7. A processing method for use in an imaging apparatus that comprises a conversion unit comprising a plurality of unit-pixels for converting, into a signal, an incident radiation or light according to the incident radiation, a control unit for controlling the conversion unit according to a plurality of operation modes, a signal processing unit, operating based on the control by the control unit, for reading a signal of unit-pixel from the conversion unit, and for reading a signal of multi-pixel derived by adding signals of two or more unit-pixels from the conversion unit, and a storage unit for storing positional information of a defective unit-pixel detected based on comparing, with a first threshold value, a signal of unit-pixel read by the signal processing unit from the conversion unit irradiated with radiation or light, and for storing positional information of a defective multi-pixel detected based on comparing, with a second threshold value, a signal of multi-pixel derived by adding signals of two or more unit-pixels read by the signal processing unit from the conversion unit irradiated with radiation or light, wherein the method comprises steps of:
performing a correction of a signal of unit-pixel read by the signal processing unit from the conversion unit, based on the positional information of the defective unit-pixel in an unit-pixel reading mode among a plurality of operation modes; and
performing a correction of a signal of multi-pixel derived by adding signals of two or more unit-pixels read by the signal processing unit from the conversion unit, based on the positional information of defective multi-pixel in a pixel-addition reading mode among a plurality of operation.

8. An imaging apparatus comprising:
a conversion unit comprising a plurality of unit-pixels for converting, into a signal, incident radiation or light according to the incident radiation or light;
a control unit for controlling said conversion unit according to a plurality of operation modes;
a signal processing unit, operating based on the control by said control unit, for reading a signal of unit-pixel from said conversion unit according to a unit-pixel reading mode among the plurality of operation modes, and for reading a signal of multi-pixel derived by adding signals of two or more unit-pixels from said conversion unit according to a pixel-addition reading mode among the plurality of operation modes;
a storage unit for storing positional information of a defective unit-pixel detected based on comparing, with a first threshold value, a signal of unit-pixel read by said signal processing unit from said conversion unit irradiated with radiation or light, and for storing positional information of a defective multi-pixel derived based on comparing, with a second threshold value smaller than the first threshold value, the signal of the unit-pixel; and
a pixel processing unit for performing a correction of a signal of a unit-pixel read by said signal processing unit from said conversion unit, based on the positional information of the defective unit-pixel in the unit-pixel reading mode, and for performing a correction of a signal of a multi-pixel derived by adding signals of two or more unit-pixels read by said signal processing unit from said conversion unit, based on the positional information of the defective multi-pixel in the pixel-addition reading mode.

9. The imaging apparatus according to claim 8, wherein the first and second threshold values are a percentage ratio to an average signal averaged signals of normal unit-pixels.

10. The imaging apparatus according to claim 8, wherein the signal of multi-pixel derived by adding signals of two or more unit-pixels read by said signal processing unit from the conversion unit is an analog signal.

11. The imaging apparatus according to claim 8, wherein said conversion unit comprises:

a wave length converter for converting incident radiation into light; and a photoelectric conversion element formed from amorphous silicon as a main ingredient.

12. A processing method for use in an imaging apparatus that comprises a conversion unit comprising a plurality of unit-pixels for converting, into a signal, incident radiation or light according to the incident radiation or light, a control unit for controlling the conversion unit according to a plurality of operation modes, a signal processing unit, operating based on the control by the control unit, for reading a signal of a unit-pixel from the conversion unit, and for reading a signal of a multi-pixel derived by adding signals of two or more unit-pixels from the conversion unit, and a storage unit for storing positional information of a defective unit-pixel detected based on comparing, with a first threshold value, a signal of a unit-pixel read by the signal processing unit from the conversion unit irradiated with radiation or light, and for storing positional information of a defective multi-pixel derived based on comparing, with a second threshold value smaller than the first threshold value, the signal of a unit-pixel, wherein the method comprises steps of:

performing a correction of a signal of a unit-pixel read by the signal processing unit from the conversion unit, based on the positional information of the defective unit-pixel in a unit-pixel reading mode among the plurality of operation modes; and performing a correction of a signal of a multi-pixel derived by adding signals of two or more unit-pixels read by the signal processing unit from the conversion unit, based on the positional information of a defective multi-pixel in a pixel-addition reading mode among the plurality of operation modes.

* * * * *